US012648898B2

(12) United States Patent
Tchakalova et al.

(10) Patent No.: US 12,648,898 B2
(45) Date of Patent: Jun. 9, 2026

(54) FORMULATIONS PROVIDING LONG-LASTING FRAGRANCE PERFORMANCE

(71) Applicant: Firmenich SA, Satigny (CH)

(72) Inventors: Vera Tchakalova, Satigny (CH); Addi Fadel, Plainsboro, NJ (US); Aude Daugeron-Jouault, Neuilly-sur-Seine (FR); Laura Mesmin, Satigny (CH); Madelyne Pham, Neuilly-sur-Seine (FR)

(73) Assignee: FIRMENICH SA, Satigny (CH)

(*) Notice: Subject to any disclaimer, the term of this patent is extended or adjusted under 35 U.S.C. 154(b) by 744 days.

(21) Appl. No.: 17/760,038

(22) PCT Filed: Feb. 2, 2021

(86) PCT No.: PCT/EP2021/052414

§ 371 (c)(1),
(2) Date: Aug. 3, 2022

(87) PCT Pub. No.: WO2021/156242

PCT Pub. Date: Aug. 12, 2021

(65) Prior Publication Data

US 2023/0098760 A1 Mar. 30, 2023

Related U.S. Application Data

(60) Provisional application No. 62/969,757, filed on Feb. 4, 2020.

(30) Foreign Application Priority Data

Aug. 25, 2020 (EP) .................................... 20192705

(51) Int. Cl.

| | |
|---|---|
| ***A61K 8/34*** | (2006.01) |
| ***A61K 8/37*** | (2006.01) |
| ***A61K 8/49*** | (2006.01) |
| ***A61Q 13/00*** | (2006.01) |

(52) U.S. Cl.

CPC ................ *A61K 8/342* (2013.01); *A61K 8/34* (2013.01); *A61K 8/37* (2013.01); *A61K 8/375* (2013.01); *A61K 8/4973* (2013.01); *A61K 8/498* (2013.01); *A61Q 13/00* (2013.01)

(58) Field of Classification Search

CPC .... A61K 8/602; A61K 8/4946; A61K 8/4973; A61K 8/375; A61K 8/342; A61K 8/345; A61K 8/34; A61K 8/498; A61K 8/92; A61K 8/37; A61L 9/01; A61L 2101/44; A61Q 13/00

USPC .......................................................... 512/2, 1

See application file for complete search history.

(56) References Cited

U.S. PATENT DOCUMENTS

| | | | | |
|---|---|---|---|---|
| 2012/0097754 | A1* | 4/2012 | Vlad ........................ | A61L 9/01 512/26 |
| 2013/0079270 | A1 | 3/2013 | Wong et al. | |
| 2014/0287982 | A1 | 9/2014 | Wong et al. | |
| 2016/0362630 | A1 | 12/2016 | Holland et al. | |
| 2017/0267943 | A1 | 9/2017 | Tchakalova et al. | |
| 2018/0180391 | A1 | 6/2018 | Holland et al. | |
| 2020/0360245 | A1† | 11/2020 | Dahms | |
| 2021/0032561 | A1† | 2/2021 | Holland | |
| 2021/0085579 | A1 | 3/2021 | Schmaus et al. | |

FOREIGN PATENT DOCUMENTS

| | | | |
|---|---|---|---|
| CN | 107847626 | A | 3/2018 |
| CN | 108888553 | A | 11/2018 |
| EP | 0616800 | A2 * | 2/1994 |
| EP | 3103523 | A1 * | 12/2016 |
| KR | 101142008 | B1 | 5/2012 |
| WO | 98/52527 | A1 | 11/1998 |
| WO | 2017/017251 | A1 | 2/2017 |

OTHER PUBLICATIONS

International Search Report and Written Opinion for corresponding International Application No. PCT/EP2021/052414 dated May 10, 2021 (17 pages).

* cited by examiner
† cited by third party

*Primary Examiner* — Jessica Whiteley

(57) ABSTRACT

The present invention provides long-lasting fragrance compositions that impart to a consumer a long-lasting perception and/or intensity of a perfume during fragrance wear. The present invention provides long-lasting fragrance compositions for prolonging the performance of a fragrance oil.

19 Claims, 17 Drawing Sheets

A

B

A

B

FORMULATIONS PROVIDING LONG-LASTING FRAGRANCE PERFORMANCE

The present application is a U.S. national phase entry under 35 U.S.C. § 371 of PCT Application No. PCT/EP2021/052414, filed Feb. 2, 2021, which claims priority to U.S. Application No. 62/969,757, filed Feb. 4, 2020, and European Patent Application No. 20192705.0, filed Aug. 25, 2020. The entire contents of these applications are explicitly incorporated herein by this reference.

FIELD OF THE INVENTION

The present invention relates to compositions and methods for providing long-lasting fragrance performance.

BACKGROUND

Maintaining fragrance intensity and/or profile over time is an important consideration for a commercial fragrance composition. In the perfumery industry there is a constant need to find new ways to prolong the intensity and perception of perfumes over time. For example, it is commonly accepted that a fragrance composition should maintain intensity and/or fragrance profile for at least 8 hours to satisfy consumer need.

Thus, it is desirable to have a fragrance composition which retains a significant portion of its initial fragrance character over time. It is also desirable that the fragrance strength of the fragrance composition remains noticeable to the consumer over long periods of time.

SUMMARY OF THE INVENTION

Formulations according to the present invention impart to consumers long-lasting perception and/or intensity of a perfume during fragrance wear with acceptable skin feel. The present invention provides long-lasting fragrance compositions, methods, and uses for prolonging the performance of a fragrance oil.

A long-lasting fragrance composition according to the present invention comprises oil, a gelator, wherein the gelator is 0.01 to 15% w/w of the long-lasting fragrance composition; a volatile solvent; and water. In certain aspects, the gelator is 0.3 to 0.6% w/w of the long-lasting fragrance composition.

A gelator of the present invention may be selected from the group consisting of: an n-alkane having a greater than 16 $CH_2$ chain, a hydroxyalkanoic acid, hydroxy-octadecanoyl, hydroxy-hexadecanoyl, a dihydroxyalkanoic acid, a dicarboxylic acid, a fatty acids alkyl ester with an alkyl chain length greater than 20 $CH_2$ groups, a hydroxyalkanoic alcohol, a glycyrrhizic acid, an anthryl derivatives, dendrimers n-alkanes, oligo(p-phenylenevinylene), dipyridylurea-carboxylic acid combination, diamine linked Dendron, dibutyl ethylhexanoyl glutamide, dibutyl lauroyl monoglycerol, dibutyl lauroyl 2-glycerol, dibutyl lauroyl glycerate, dibutyl lauroyl glyceryl ether, dibutyl lauroyl monoethanolamide, dibutyl lauroyl diethanolamide, dibutyl lauroyl glutamide, an organogelator, an amino acid-based gelator, a hydroxyfatty acid gelator, an ester gum, hydroxypropyl cellulose, and combinations thereof.

In aspects of the present invention, the long-lasting fragrance composition includes a fragrance oil, a gelator and an amphiphilic oil-soluble compound. The amphiphilic oil-soluble compound may be 0.01% to 40% w/w of the long-lasting fragrance composition. In other aspects, the amphiphilic oil-soluble compound is 0.5% to 30% w/w of the long-lasting fragrance composition.

The amphiphilic oil-soluble compound of the present invention includes a compound having one of the following chemical structures:

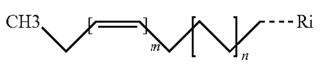

or

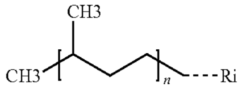

where n represents the number of $CH_2$ groups and is greater than 14 and m represents the number of unsaturated C—C bounds and is greater than or equal to 1, and Ri is selected from the group consisting of:

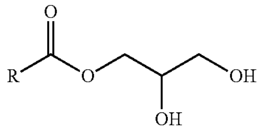

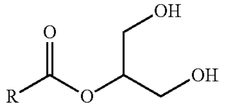

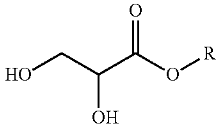

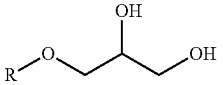

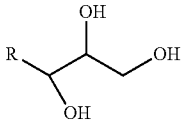

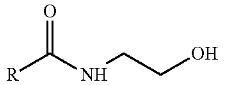

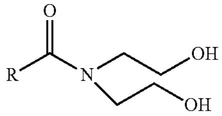

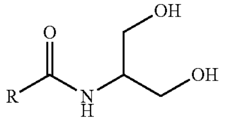

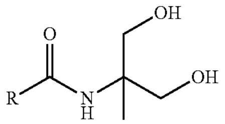

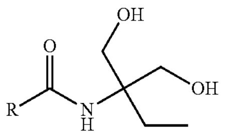

-continued

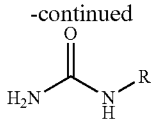

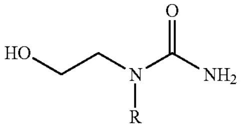

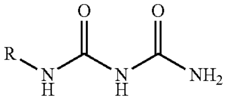

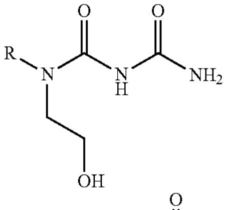

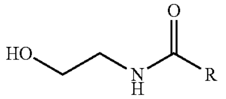

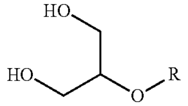

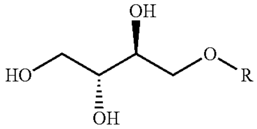

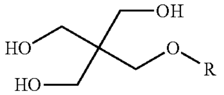

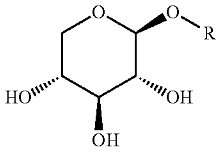

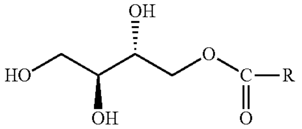

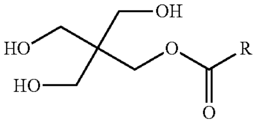

serinolamide, methylpropanediolamide, ethylpropanediolamide, urea, a urea alcohol, biuret, a biuret alcohol, anandamine, glycerol ether, a glycolipid, and a combination thereof.

In certain aspects, the amphiphilic oil-soluble compound is glycerol monooleate or phytantriol or combination thereof.

A long-lasting fragrance composition of the present invention may comprise 0.01% to 40% w/w of an amphiphilic oil-soluble compound, a volatile solvent, and water. The amphiphilic oil-soluble compound may be 0.5 to 10% w/w of the long-lasting fragrance composition.

A fragrance oil may comprise from 0.01 to 70% w/w of the long-lasting fragrance composition.

A long-lasting fragrance composition according to the present invention may comprise a fragrance oil, 0.01% to 40% w/w of the long-lasting fragrance composition of an amphiphilic oil-soluble compound, a volatile solvent, and water. In certain aspects, the amphiphilic oil-soluble compound is 0.5 to 10% w/w of the long-lasting fragrance composition.

In aspects of the present invention the water is 0.01 to 60% w/w of the long-lasting fragrance composition. In other aspects, the water is 0.7%-60% w/w of the long-lasting fragrance composition. In aspects of the invention, the water content may be 0.1 to 60% w/w of the long-lasting fragrance composition; 0.7 to 50% w/w of the long-lasting fragrance composition; or 1% to 30% w/w of the long-lasting fragrance composition.

The volatile solvent may be, for example, ethanol, isopropyl alcohol, an ether, or mixtures thereof.

A long-lasting fragrance composition of the present invention may further include a modulator. In aspects of the invention, the modulator may be selected from the group consisting of: methyl glucoside polyol; ethyl glucoside polyol; propyl glucoside polyol; isocetyl alcohol; PPG-3 myristyl ether; neopentyl glycol diethylhexanoate; sucrose laurate; sucrose dilaurate, sucrose myristate, sucrose palmitate, sucrose stearate, sucrose distearate, sucrose tristearate, hyaluronic acid disaccharide sodium salt, sodium hyaluronate, propylene glycol propyl ether; dicetyl ether; polyglycerin-4 ethers; isoceteth-5; isoceteth-7, isoceteth-10; isoceteth-12; isoceteth-15; isoceteth-20; isoceteth-25; isoceteth-30; disodium lauroamphodipropionate; hexaethylene glycol monododecyl ether; and their mixtures; neopentyl glycol diisononanoate; cetearyl ethylhexanoate; panthenol ethyl ether, DL-panthenol, N-hexadecyl n-nonanoate, noctadecyl n-nonanoate, nerolidol, polymethylol a profragrance, cyclodextrin, an encapsulation, and a combination thereof.

In some aspects, the modulator comprises 0.5% to 20% w/w of the total weight of the long-lasting fragrance composition. In an aspect of the present invention, the modulator comprises 1% w/w of the total weight of the long-lasting fragrance composition. In a further aspect, the modulator comprises 2% w/w of the total weight of the long-lasting fragrance composition. In another aspect, the modulator comprises 3% w/w of the total weight of the long-lasting fragrance composition. In further aspects, the modulator may comprise 4% or 5% w/w of the total weight of the long-lasting fragrance composition.

In aspects of the invention, the amphiphilic oil-soluble compound has one of the following chemical structures:

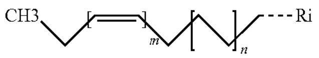

or

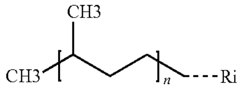

where n represents the number of CH2 groups and is greater than 14 and m represents the number of unsaturated C—C bounds and is greater than or equal to 1, and Ri is selected from the group consisting of:

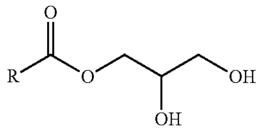

-continued

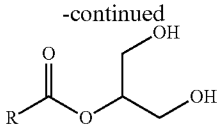

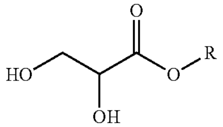

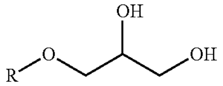

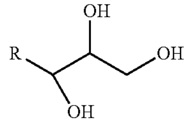

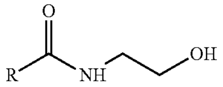

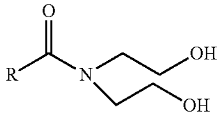

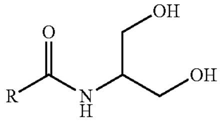

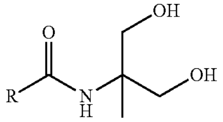

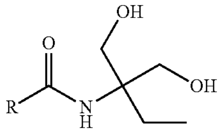

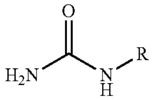

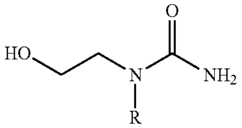

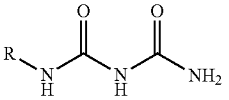

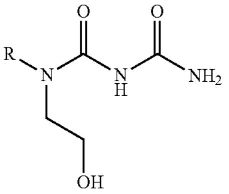

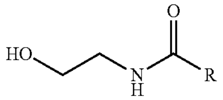

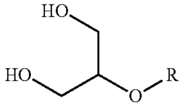

-continued

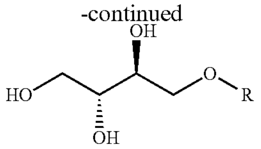

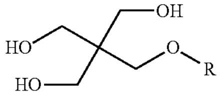

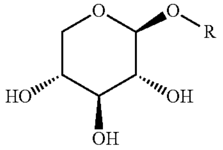

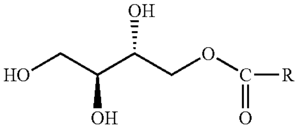

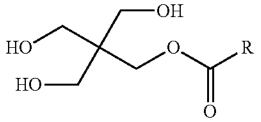

serinolamide, methylpropanediolamide, ethylpropanediolamide, urea, a urea alcohol, biuret, a biuret alcohol, anandamine, glycerol ether, a glycolipid, and a combination thereof.

In certain aspects, the amphiphilic oil-soluble compound is glycerol monooleate or phytantriol or a combination thereof. In some embodiments, the amphiphilic oil-soluble compound comprises from 1% to 5% w/w of the total weight of the long-lasting fragrance composition. In another embodiment, the amphiphilic oil-soluble compound comprises about 3% of the total weight of the long-lasting fragrance composition.

In aspects of the invention, 40 to 100% of the fragrance oil in the long-lasting fragrance composition is a volatility component comprising at least one perfume raw material having a vapor pressure greater than 0.0008 Torr at 22° C. In a further aspect, the volatility component comprises at least one perfume raw material having a vapor pressure greater than 0.08 torr.

The long-lasting fragrance composition may further comprise a second perfume raw material having a vapor pressure greater than 0.08 Torr at 22° C.

In aspects, 0.08 to 85% of the fragrance oil in the long-lasting fragrance composition is a volatility component comprising at least one perfume raw material having a vapor pressure in the range of 0.0008 to 0.08 Torr at 22° C. The long-lasting fragrance composition may further comprise a second perfume raw material having a vapor pressure in the range of 0.0008 to 0.08 Torr at 22° C.

The present invention encompasses a leave-on volatile solvent-containing consumer product comprising a long-lasting fragrance composition. The leave-on volatile solvent containing consumer product may be Parfum, Eau de Toilette, Eau de parfum, Eau de Cologne, Body mist, body spray, Body splash, Hair mist, air care spray, Hair Leave products, Fabric refreshers, and Deodorant.

The leave-on volatile solvent containing consumer product may further comprise a dye, a UV filters, an antioxidant, a quencher, a chelating agent, a solubilizer, a moisturizer, a humectant, an anti-aging active, a soothing agent, emollients, an anti-pollution active, or a combination thereof.

DETAILED DESCRIPTION

Figure 1:
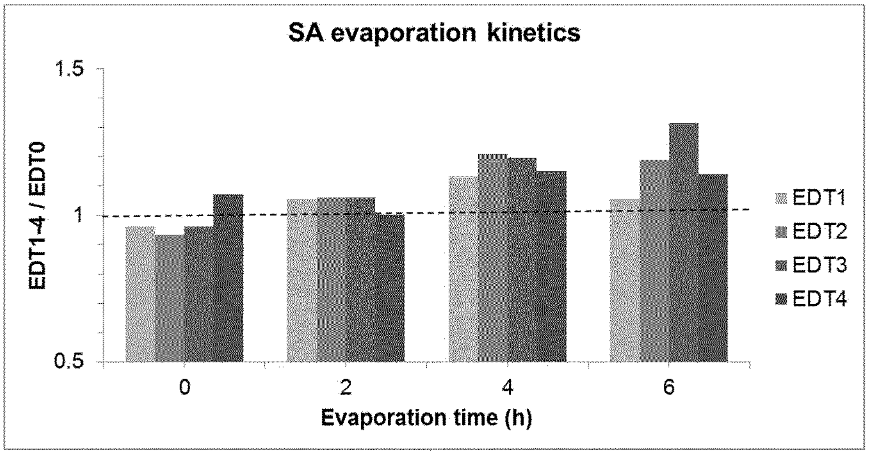
FIG. 1 is a bar graph showing the relative intensity of fragrance ingredient styrallyl acetate, solubilized in the formulations EDT 1-4 in the head space at different moments of evaporation.

The present invention provides compositions that prolong the performance of a fragrance oil. A "long-lasting fragrance composition" as used herein means that a fragrance oil according to the present invention has prolonged performance relative to the fragrance oil alone. Prolonged performance may be measured by methods known in the art. For example, by quantitative GC-MS analysis following evaporation kinetics; by sensory panels rating over all intensity or rating olfactive attributes.

The present invention provides compositions that improve fragrance performance by imparting consumer-perceived long-lasting perception of a perfume during fragrance wear while maintaining a clear, transparent, sprayable and stable hydro-alcoholic formulation and solution with an acceptable skin feel.

A long-lasting fragrance composition of the present invention is suitable for volatile solvent (ethanol, for example)-containing consumer fragrance products for the skin or hair. In an embodiment, a long-lasting fragrance composition of the present invention may be dispensed using an atomizer in a micronized mist, which will enhance the fragrance performance thanks to the use of a dispensing system composed of a multichannel nozzle.

A long-lasting fragrance composition of the present invention can be diluted by a solvent (e.g., ethanol)—water mixture in order to obtain a final consumer product such as a Parfum, Eau de toilette, Eau de parfum, Body-mist, Body spray, Body splash, deodorant, Hair mist, lotion, air care products, and other solvent-based consumer products. Optionally the long-lasting fragrance composition can be coupled with non-odoriferous fragrance modulators, odoriferous fragrance modulators, entrapment macromolecule like cyclodextrins, and/or profragrances in order to enhance the long-lasting benefits.

A composition according to the present invention may include: A) hydrophobic active such as a fragrance oil; B) an amphiphilic oil-soluble compound; C) a volatile solvent (such as ethanol) having an evaporation rate or a vapor pressure higher than that of water (VP=3.17 kPa at 25° C. and 5.62 kPa at 35° C.); D) water; E) a low molecular weight gelator and optionally F) a hydroptopic salt.

An amphiphilic oil-soluble compound of the present invention includes a compound having one of the following chemical structures:

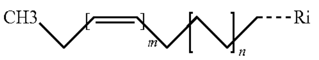

or

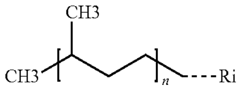

where n represents the number of CH2 groups and is greater than 14, m represents the number of unsaturated C—C bounds and is greater than or equal to 1, and Ri is one or a combination of the following groups:

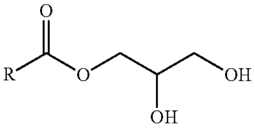

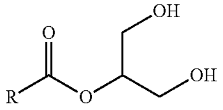

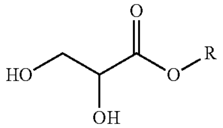

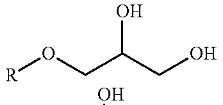

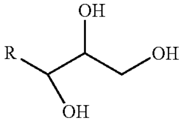

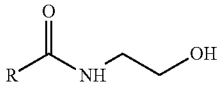

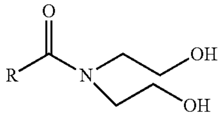

-continued

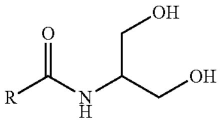

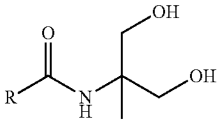

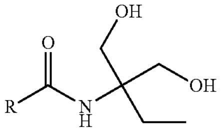

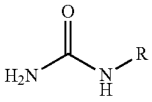

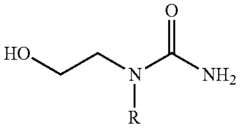

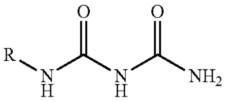

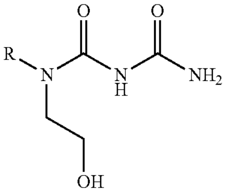

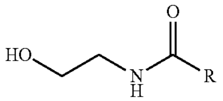

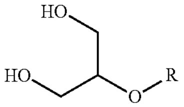

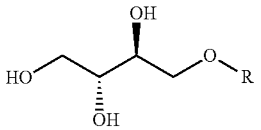

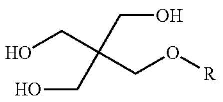

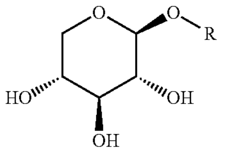

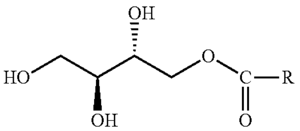

-continued

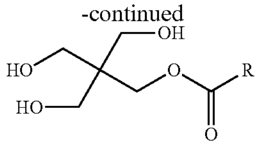

serinolamide, methylpropanediolamide, ethylpropanediolamide, urea, a urea alcohols, biuret, a biuret alcohol, anandamine, glycerol ether, and/or a glycolipid. The amphiphilic oil-soluble compound is soluble in the volatile solvent, not soluble or slightly soluble in water, and has a packing parameter >1.

In certain aspects, the amphiphilic oil-soluble compound is glycerol monooleate, phytantriol, a long chain fatty acid ($CH_2$ greater than 14), or a surfactant with a hydrophilic-lipid balance (HLB) less than 10.

An amphiphilic oil-soluble compound may be a surface active compound such as a surfactant having a HLB<10, long-chained fatty acids and fatty alcohols having CH2>14 such as myristyl, palmityl, oleyl, docosanoyl, and others.

A "fragrance oil" according to the present invention includes fragrance, fragrance ingredients, essential oils, and a mix of aroma compounds and natural ingredients such as essential oils, extracts, and resins.

The fragrance oil may be 0.01% to 80% w/w of the long-lasting fragrance composition. In an aspect of the invention, the fragrance oil may be 1% to 30% w/w of the long-lasting fragrance composition.

A gelator (gelling agent) according to the present invention may be a molecule from the class of Low Molecular Weight Gelators (LMWG) compounds such as long chain (>16$CH_2$) n-alkanes, hydroxyalkanoic acids as hydroxy-octadecanoyl, hydroxy-hexadecanoyl, etc., dihydroxyalkanoic acids, dicarboxylic acids, fatty acids alkyl ester with alkyl chain length >20 CH2 groups, hydroxyalkanoic alcohols, steroid derivatives such as glycyrrhizic acid, caffeine, anthryl derivatives, molecules containing steroidal and condensed aromatic rings, dendrimers n-alkanes, oligo(p-phenylenevinylene), dipyridylurea—carboxylic acid combination, diamine linked Dendron, amino acid-based gelators such as dibutyl ethylhexanoyl glutamide and dibutyl lauroyl monoglycerol, 2-glycerol, glycerate, glyceryl ether, monoethanolamide, diethanolamide, glutamide, carbohydrate derived gelators, peptide-based derivatives, and others. Preferred gelators are organogelators. Preferred gelators are amino acid-based gelators and hydroxyfatty acid gelators.

A volatile solvent according to the present invention has an evaporation rate or vapor pressure higher than that of water. The vapor pressure of water at 35° C. is 5.62 kPa. In one aspect of the present invention, the volatile solvent is ethanol.

A long-lasting fragrance of the present invention may include a hydrotrope or hydrotropic salt (e.g., sodium salicylate). Suitable ranges of a hydrotrope or hydrotropic salt are 0 to 5% w/w of the long-lasting fragrance, or 0.01% to 2% w/w of the long-lasting fragrance.

A long-lasting fragrance composition of the present invention may include an osmolyte. An osmolyte may be a slightly water soluble compound such as a humectant (e.g., glycols such as dipropylene glycol, butylene glycol, propylene glycol, glycerine, pentanediols, hexanediols, propanediols, butanediols, xylitol), an emollient, a natural osmolyte (ectoine), and a biopolymer. The osmolyte may be 0 to 1% or 0.01% to 0.5% w/w of the long-lasting fragrance.

Consumer Products:

Leave-on volatile solvent containing consumer products such as Parfum, Eau de Toilette, Eau deparfum, Body mist, body spray, Body splash, Hair mist, air care spray, Hair Leave-on products, Fabric refreshers, Deodorant, etc.

The leave-on volatile solvent containing consumer product may further include a dye, a UV filters, an antioxidant, a quencher, a chelating agent, a solubilizer, a moisturizer, a humectant, an anti-aging active, a soothing agent, an anti-pollution active, emollient or a combination thereof.

EXAMPLES

The following examples illustrate, but do not limit, the present invention.

Example 1: Reference EDT (EDT0)

a) Formulation and Process

A reference Eau De Toilette (EDT) formulation was prepared and used as a reference to evaluate fragrance performance. Water was added to ethanol as set forth in Table 1. After stirring, fragrance was added to this solution. The final mixture was stirred until homogeneous.

TABLE 1

| Ingredients | Amount (% wt) | Function |
|---|---|---|
| Ethanol [1)] | 70 | Solvent |
| Water | 20 | Solvent |
| Fragrance | 10 | Fragrance |

[1)] Ethanol Absolute anhydrous; origin: Carlo Erba.

Example 2: EDT Containing Phytantriol (EDT1)

b) Formulation and Process

The amphiphilic oil-soluble compound phytantriol was dissolved in ethanol. Water was added to this solution. After stirring, fragrance was added to this mixture. The final solution was stirred until homogeneous. See Table 2.

TABLE 2

| Ingredients | Amount (% wt) | Function |
|---|---|---|
| Ethanol[1)] | 70 | Solvent |
| Water | 19 | Solvent |
| Phytantriol[2)] | 1 | Amphiphilic oil soluble compound |
| Fragrance | 10 | Fragrance |

[1)]Ethanol Absolute anhydrous; product of Carlo Erba.
[2)]3,7,11,15-Tetramethylhexadecane-1,2,3-triol (Phytantriol) product of DSM.

Example 3: EDT Containing Phytantriol and Glycyrrhizic Acid Ammonium Salt (AGA) (EDT2)

a) Formulation and Process

Phytantriol and Glycyrrhizic acid ammonium salt were mixed in ethanol. To this solution was added water. After stirring, fragrance was added to this mixture. The final solution was stirred until homogeneous. See Table 3.

TABLE 3

| Ingredients | Amount (% wt) | Function |
|---|---|---|
| Ethanol[1)] | 70 | Solvent |
| Water | 19 | Solvent |

TABLE 3-continued

| Ingredients | Amount (% wt) | Function |
|---|---|---|
| Phytantriol[2)] | 0.75 | Amphiphilic oil soluble compound |
| Glycyrrhizic acid ammonium salt[3)] | 0.25 | Gelator |
| Fragrance | 10 | Fragrance |

[1)]Ethanol Absolute anhydrous; origin: Carlo Erba.
[2)]Phytantriol; origin: DSM.
[3)]Glycyrrhizic acid ammonium salt from glycyrrhiza root (licorice); origin: Sigma-Aldrich.

Example 4: EDT Containing Phytantriol and Caffeine (EDT3)

a) Formulation and Process

Phytantriol and caffeine were mixed in ethanol. To this solution was added water. After stirring, fragrance was added to this mixture. The final solution was stirred until homogeneous. See Table 4.

TABLE 4

| Ingredients | Amount (% wt) | Function |
|---|---|---|
| Ethanol[1)] | 70 | Solvent |
| Water | 19 | Solvent |
| Phytantriol[2)] | 0.75 | Amphiphilic oil soluble compound |
| Caffeine[3)] | 0.25 | Gelator |
| Fragrance | 10 | Fragrance |

[1)]Ethanol Absolute anhydrous; origin: Carlo Erba.
[2)]Phytantriol; origin: DSM.
[3)]Caffeine; origin: Fluka Analytical.

Example 5: EDT Containing Phytantriol and Sodium Salicylate (EDT4)

a) Process

Phytantriol and sodium salicylate were mixed in Ethanol. To this solution was added water. After stirring, fragrance was added to this mixture. The final solution was stirred until homogeneous. See Table 5.

TABLE 5

| Ingredients | Amount (% wt) | Function |
|---|---|---|
| Ethanol[1)] | 70 | Solvent |
| Water | 18.8 | Solvent |
| Phytantriol[2)] | 1 | Amphiphilic oil soluble compound |
| Sodium Salicylate[3)] | 0.2 | Hydrotropic salt |
| Fragrance | 10 | Fragrance |

[1)]Ethanol Absolute anhydrous; origin: Carlo Erba.
[2)]Phytantriol; origin: DSM.
[3)]Sodium Salicylate, 99%; origin: Alfa Aesar.

Example 6: EDT Containing Glycerol Monooleate

Glycerol monooleate (GMO) was mixed in ethanol. To this solution was added water. After stirring, fragrance was added to this mixture. The final solution was stirred until homogeneous. See Table 6.

TABLE 6

| Ingredients | Amount (% wt) | Function |
|---|---|---|
| Ethanol[1)] | 72 | Solvent |
| Water | 15 | Solvent |
| Glycerol monooleate[2)] | 3 | Structuring amphiphilic oil soluble compound |
| Fragrance | 10 | Fragrance |

[1)]Ethanol Absolute anhydrous; origin: Carlo Erba.
[2)]Glycerol monooleate; origin: Dupont.

Example 7: EDT Containing Isocetyl Alcohol

Isocetyl alcohol (ICA) was mixed in ethanol. To this solution was added water. After stirring, fragrance was added to this mixture. The final solution was stirred until homogeneous. See Table 7.

TABLE 7

| Ingredients | Amount (% wt) | Function |
|---|---|---|
| Ethanol[1)] | 70 | Solvent |
| Water | 15 | Solvent |
| Isocetyl alcohol[2)] | 5 | Modulator |
| Fragrance | 10 | Fragrance |

[1)]Ethanol Absolute anhydrous; origin: Carlo Erba.
[2)]Isocetyl alcohol; origin: Ashland.

Example 8: EDT Containing Glycerol Monooleate and Isocetyl Alcohol

Glycerol monooleate (GMO) and isocetyl alcohol (ICA) were mixed in Ethanol. To this solution was added water. After stirring, fragrance was added to this mixture. The final solution was stirred until homogeneous. See Table 8.

TABLE 8

| Ingredients | Amount (% wt) | Function |
|---|---|---|
| Ethanol[1)] | 67 | Solvent |
| Water | 15 | Solvent |
| Glycerol monooleate[2)] | 3 | Amphiphilic oil soluble compound |
| Isocetyl alcohol[3)] | 5 | Modulator |
| Fragrance | 10 | Fragrance |

[1)]Ethanol Absolute anhydrous; origin: Carlo Erba.
[2)]Glycerol monooleate; origin: Dupont.
[3)]Isocetyl alcohol; origin: Ashland.

Example 9: EDT Containing Glycerol Monooleate, Nerolidol and Dibutyl Ethylhexanoyl Glutamide Glycerol monooleate (GMO), nerolidol and dibutyl ethylhexanoyl glutamide (EB-21) were mixed in ethanol. To this solution was added water. After stirring, fragrance was added to this mixture. The final solution was stirred until homogeneous. See Table 9.

TABLE 9

| Ingredients | Amount (% wt) | Function |
|---|---|---|
| Ethanol | 70.70 | Solvent |
| Water | 15 | Solvent |

TABLE 9-continued

| Ingredients | Amount (% wt) | Function |
|---|---|---|
| Glycerol monooleate | 3 | Amphiphilic oil soluble compound |
| Nerolidol | 1 | Modulator |
| Dibutyl Ethylhexanoyl Glutamide | 0.3 | Gelator |
| Fragrance | 10 | Fragrance |

Example 10: EDT Containing Glycerol Monooleate, Nerolidol, Polymethylol and Dibutyl Ethylhexanoyl Glutamide Glycerol monooleate (GMO), nerolidol, polymethylol and dibutyl ethylhexanoyl glutamide (EB-21) were mixed in ethanol. To this solution was added water. After stirring, fragrance was added to this mixture. The final solution was stirred until homogeneous. See Table 10.

TABLE 10

| Ingredients | Amount (% wt) | Function |
|---|---|---|
| Ethanol | 69.70 | Solvent |
| Water | 15 | Solvent |
| Glycerol monooleate | 3 | Amphiphilic oil soluble compound |
| Nerolidol | 1 | Modulator |
| Polymethylol | 1 | Modulator |
| Dibutyl Ethylhexanoyl Glutamide | 0.3 | Gelator |
| Fragrance | 10 | Fragrance |

Example 11: EDT Containing Glycerol Monooleate, Nerolidol, Polymethylol and Dibutyl Ethylhexanoyl Glutamide Glycerol monooleate (GMO), polymethylol and dibutyl ethylhexanoyl glutamide (EB-21) were mixed in Ethanol. To this solution was added water. After stirring, fragrance was added to this mixture. The final solution was stirred until homogeneous. See Table 11.

TABLE 11

| Ingredients | Amount (% wt) | Function |
|---|---|---|
| Ethanol | 69.70 | Solvent |
| Water | 15 | Solvent |
| Glycerol monooleate | 3 | Amphiphilic oil soluble compound |
| Polymethylol | 2 | Modulator |
| Dibutyl Ethylhexanoyl Glutamide | 0.3 | Gelator |
| Fragrance | 10 | Fragrance |

Example 12—Performance a) Process

Evaporation kinetic studies were performed. The test and reference compositions were deposited on the glass bottom of head-space vials and were evaporated after 2, 4, 6 or sometimes 24 hours at 32° C. (corresponding to the skin temperature) under agitation. At a given moment, the vials were closed and left for saturation of the head-space at 32° C. Small amounts of the saturated head-space vapors were injected in GC-MS instrument and the vapor composition was analyzed.

Sample Preparation

For kinetics analysis, six identical samples were prepared at the same time. For each sample, a piece (1×1 cm) of blotter (Scentis, 160 mm×20 mm) was introduced at the bottom of a 20 mL headspace-GCMS screw vial (BGB Analytik, 180420). 10 μL of an EDT-type sample was deposited on the blotter with a micropipette. All vials were closed after the required evaporation time (0, 2, 4 or 6 h).

A CTC PAL was installed on the GC-MS (6890 series GC system & 5973 network MS) for sample injection. This CTC PAL was equipped with a 1 mL syringe. 1 mL of headspace gas was taken from the samples and injected into a GC-MS instrument. Before each injection, samples were agitated at 32° C. for 30 min by the composer of the GCMS.

GC Parameters

An Agilent GC was used with a split/splitless inlet and Helium as carrier gas. A septum BTO was installed (Bleed & Temp Optimized septa, 11 mm/Agilent 5183-4757) and the liner was heated at 250° C. (liner, splitless, single traper, deactivated/Agilent 5181-3316). The samples were analyzed with a split ratio 5:1.

A non-polar column was mounted in the oven. (Agilent_190915-433_HP-5MS—Fused silica capillary column-bounded, PDMS ((5%-Phenyl)-methylpolysiloxane—Length 30 m, diameter 250 μm, Film thickness 0.25 μm). The analyses were done at constant flow with an initial flow at 1 mL/min (corresponding to an average velocity of 36 cm/s). The oven program started at 40° C. The temperature rose to 150° C. with a temperature ramp of 20° C./min, and then rose to 250° C. with a temperature ramp of 50° C./min. The oven held the temperature at 250° C. for one minute.

MS Parameters—SIM Method

A SIM method was used to determine fragranced ingredients in headspace gas. No solvent delay was used. The mass were analyzed between 35 and 320 with a threshold at 25.

b) Results

1) Single Perfumery Ingredient Performance

The perfumery ingredient Styrallyl acetate (provided by Firmenich SA and having a volatility equal to 1320.4 μg/L air) was solubilized in formulation EdT1-4 and deposited according to "Sample preparation" above. Performance at different times during the evaporation process is shown in FIG. 1 as value relative to the intensity of the reference EdT formulation. The results demonstrate increased fragrance performance from formulations EDT1 to 4 after 2 and, even greater, after 4 hours of evaporation compared to the reference sample (EDT0) corresponding to 1.

2) Model Perfumery Mixture Performance

Figure 2:
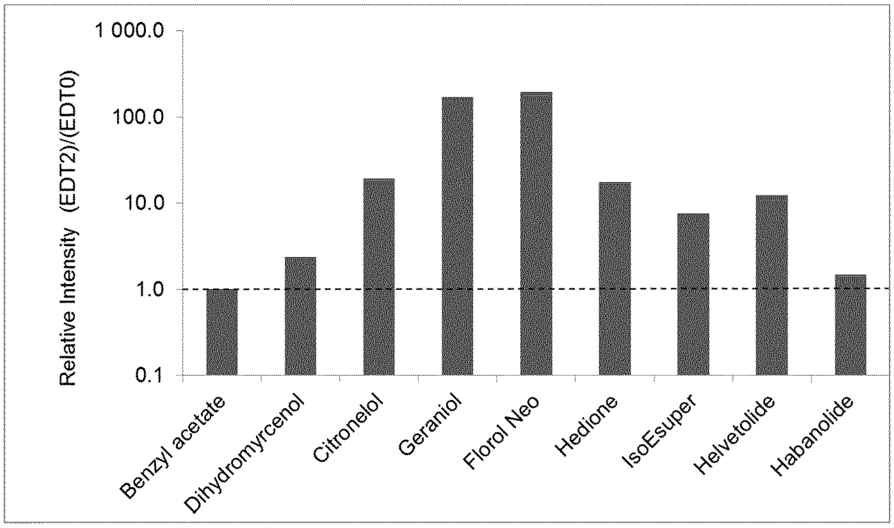
FIG. 2 is a bar graph showing the relative intensity of fragrance A ingredients after 6 h of evaporation from formulations EDT2 (with gelator AGA)

Test 1:

Model fragrance A, shown in Table 12, was solubilized in EDT2 and deposited as explained in "Sample preparation". The intensity of the perfumery ingredients, was followed at different times during the evaporation process. The performance of the perfumery ingredients 6 hours after the deposition is shown in FIG. 2 as value relative to the intensity of the reference EdT formulation. The values >1 mean that the intensity was greater than the reference EdT0.

TABLE 12

| Fragrance A | | |
|---|---|---|
| Fragrance Ingredient | % wt | Volatility (μg/L air) |
| Benzyl Acetate | 6 | 2016.3 |
| Dihydromyrcenol Pur | 2 | 252.3 |
| Citronellol BJ | 2 | 189.61 |
| Florol Neo | 12 | 176.08 |
| Geraniol Pur | 10 | 148.42 |
| Hedione | 10 | 19.33 |
| Phenethylol Ord | 20 | 12.78 |
| Iso E Super | 2 | 10.05 |
| Helvetolide | 4 | 6.68 |
| Muscenone delta | 1 | 5.24 |
| Habanolide | 6 | 0.9053 |
| Dipropylene Glycol* | 25 | |

Test 2:

TABLE 13

Research Accord HT1 (RAHT1) used in this experiment consists of below 44 ingredients ranging from high volatility to low volatility ingredients at equal concentrations.

| Compound Name | VOLATILITY μg/l air | LOG Po/w |
|---|---|---|
| PIPOL ACETATE | 5880 | 2.62 |
| ALLYL CAPROATE | 2750 | 3.62 |
| ZESTOVER | 2060 | 2.34 |
| 3-Cyclohexene-1-carboxylic acid, 2,6,6-trimethyl-, methyl ester | 1880 | 3.63 |
| OXANE | 1840 | 3.11 |
| PIPOL BUTYRATE | 1670 | 3.59 |
| METHYL BENZOATE | 1610 | 2.1 |
| ROMASCONE | 1460 | 3.93 |
| ETHYL BENZOATE | 1290 | 2.51 |
| DIMETOL | 1150 | 3.24 |
| PIPOL ISOBUTYRATE | 1070 | 3.57 |
| Propyl (2S)-2-(1,1-dimethylpropoxy)-propanoate | 995 | 3.17 |
| GALBANOLENE SUPER | 994 | 5.68 |
| SAFRANAL | 918 | 2.57 |
| LINALOL BJ | 899 | 2.94 |
| ISOBORNYL ACETATE PUR | 886 | 4.13 |
| MENTHONE PURIFIED | 839 | 3.46 |
| ALLYL HEPTANOATE | 822 | 4.16 |
| CITRONELLALCP | 771 | 2.91 |
| TRANS DECENAL | 691 | 3.73 |
| VIOLETTYNE 10 MIP(1,3-Undecadien-5-yne) | 677 | 5.11 |
| KOAVONE | 659 | 3.71 |
| ESTRAGOLE | 587 | 3.33 |
| PHENYLETHYL FORMATE | 568 | 1.9 |
| ETHYL LINALOL | 343 | 3.54 |
| DELPHONE | 235 | 3.62 |
| DELTA DAM ASCON E | 151 | 4.13 |
| CITRONELLYL ACETATE | 129 | 4.22 |
| NERYL ACETATE BJF | 123 | 3.81 |
| Methyl Octyl Carbinol (OCM) | 91.8 | 3.51 |
| GERANYL ACETATE EXTRA | 85.2 | 3.99 |
| ALLYL CYCLOHEXYLPROPIONATE | 44 | 4.51 |
| INDOLE | 33.1 | 1.74 |
| MAGNOLAN | 32.5 | 2.44 |
| GAMMA NONALACTONE | 27.4 | 2.45 |
| CYCLOSAL | 24.2 | 3.59 |
| DECAL | 9.63 | 3.02 |
| UNDECALACTONE DELTA | 4.64 | 3 |
| 5-Cyclopentadecen-1-one, 3-methyl | 2.49 | 5.98 |
| Naphtho[2,1-b]furan, dodecahydro-3a,6,6,9a-tetramethyl-, [3aR | 2.19 | 6.88 |
| VANILLIN PERF | 2.19 | 0.72 |
| (+)-cis-METHYL DIHYDROJASMONATE | 1.63 | 2.95 |
| COUMARIN | 0.51 | 1.35 |
| BENZYL SALICYLATE | 0.26 | 4.26 |

Tables 14A-C. Below are the three formulas tested—model perfume (RAHT1 in EDT) as control, technology 1 as model perfume with 5% Phytantriol 2% Polymethylol 0.3% EB-21 gelling agent and technology 2 as model perfume with 5% Phytantriol 2% Schercemol 0.3% EB-21 gelling agent.

| A | | |
|---|---|---|
| Model perfume as control | Quantity (% wt) | Quantity (g) |
| Research Accord HT1 | 10.00% | 1 |
| EtOH 40B | 80.00% | 8 |
| H2O | 10.00% | 1 |
| Total | 100.00% | 10 |

| B Technology 1: Model perfume + 5% Phytantriol + 2% Polymethylol + 0.3% EB-21 | | |
|---|---|---|
| | Quantity (% wt) | Quantity (g) |
| Research Accord HT1 | 10.00% | 1 |
| Phytantriol | 5.00% | 0.5 |
| EB-21 | 0.30% | 0.03 |
| Polymethylol | 2.00% | 0.2 |
| EtOH 40B | 67.70% | 6.77 |
| H2O | 15.00% | 1.5 |
| Total | 100.00% | 10 |

| C Technology 2: Model perfume + 5% Phytantriol + 2% Schercemol + 0.3% EB-21 | | |
|---|---|---|
| | Quantity (% wt) | Quantity (g) |
| Research Accord HT1 | 10.00% | 1 |
| Phytantriol | 5.00% | 0.5 |
| EB-21 | 0.30% | 0.03 |
| Schercemol | 2.00% | 0.2 |
| EtOH 40B | 67.70% | 6.77 |
| H2O | 15.00% | 1.5 |
| Total | 100.00% | 10 |

Method Used as Follows:

Evaporations were done in Tzero lids. Prazitherm PZ72 slide warmer was pre-heated to 32 degrees Celsius for 30 minutes. Each crucible was placed on the precision hotplate. Using an adjustable volume pipette, 10 μL of fragrance was dosed directly to the center of the crucible and evaporated at 32° C. for 1 hour, 2 hours, 4 hours and 6 hours on the precision hotplate. A duplicate set was performed for each sample and each condition tested. When time points were reached, each crucible was placed in a 2-mL Agilent GC vial (Agilent 5183-2068) and 600 μL ethanol was added to stop the evaporation. Vials were closed and mixed by shaking for at least 1 minute. Samples were analyzed by GC-MS direct injection methodology. See FIGS. 8 to 17.

3) Effect of Amphiphilic Oil-Soluble Compound Concentration

Figure 3:
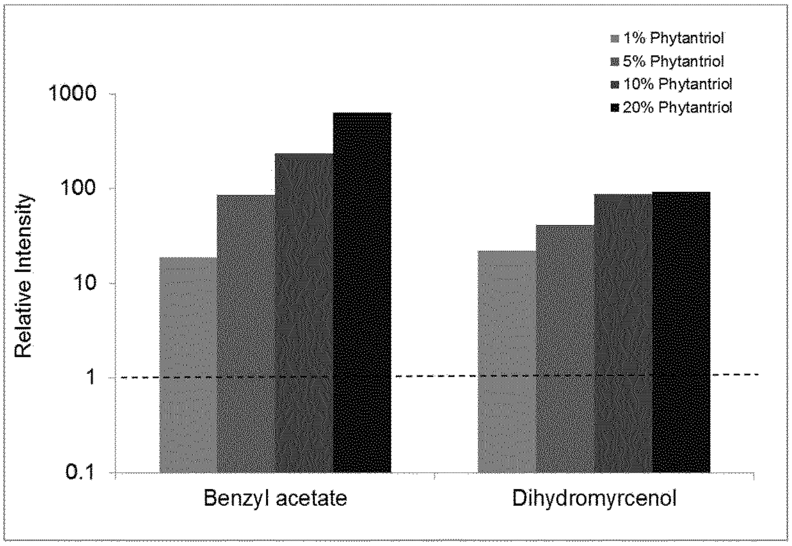
FIG. 3 is a bar graph showing the effect of compound concentration on fragrance retention after 6 hours evaporation at 32° C.

The effect of the amphiphilic oil-soluble compound concentration on the retention of fragrance ingredients is shown in FIG. 3. Fragrance A was solubilized at 10% wt in a mixture of ethanol, water, phytantriol at different phytantriol concentrations. The water concentration was kept constant and equal to 20% wt. Increasing phytantriol concentration lead to better results; after 6 hours of evaporation, the highly volatile benzyl acetate and dihydromyrcenol had higher concentrations in the head space in comparison to the reference sample.

4) Sensory Evaluation in the Presence of Phytantriol or Glycerol Monooleate or Mixtures A sensory evaluation of fragrance intensity was performed. 20 μl of formulation was deposited on glass plates, which were maintained at 32° C. on a heated platform. At different times (t=0 min (Fresh), 2 hours, 4 hours, 5 hours and 6 hours), the randomized glass plates were evaluated by 15 panelists.

A 3-Alternative Forced Choice (or 3-AFC) test was used. For each time point, panelists were presented with 3 samples, two of which were the fragrance (SP), and one in which the fragrance was in accordance with the present invention. Panelists indicated the sample(s) that were higher in terms of overall intensity.

Hypothesis:

H0: The two samples are not different.

H1: The sample with technology is more intense than the sample without it, in terms of overall intensity.

Associated Risks:

H0 rejected=a risk:

Risk associated with a false alarm, concluding that products differ when in fact they do not.

Data was analyzed using the binomial statistic.

Data Interpretation:

If the p-value obtained for $\alpha \leq 0.05$, then the sample with technology was more intense in overall intensity than the sample without it If the p-value obtained for $\alpha$ is $0.05 < \alpha \leq 0.10$, then a trend difference was determined.

If the p-value obtained for $\alpha > 0.10$, the samples were not significantly different.

The fragrance SP contained 44% of fragrance ingredients with log P<4 (high volatility).

The results of the sensory panel presented in Table 15 shows the higher performance of the formulation according to the present invention after 4 hours of evaporation in the presence of 10% phytantriol, and after 2 hours of evaporation in the presence of 10% GMO.

TABLE 15

| Samples | Nb of panelists | p-value Fresh | 2 h | 4 h | 5 h | 6 h |
|---|---|---|---|---|---|---|
| SP @10% (ref) vs SP @ 10% + 10% Phytantriol | 16 | 0.4531 | 0.1265 | 0.0008 | 0.0008 | 0.0500 |
| SP @10% (ref) vs SP @ 10% + 10% GMO | 16 | 0.2630 | 0.0160 | 0.0040 | 0.0040 | 0.0160 |

The performance of mixtures of GMO with ICA was studied.

Sensory panels were performed in order to compare:

Fragrance SP in EDT without and with 3% GMO (Table 6),

Fragrance SP in EDT without and with 5% ICA (Table 7),

Fragrance SP in EDT without and with 3% GMO+5% ICA (Table 8).

Figure 4:
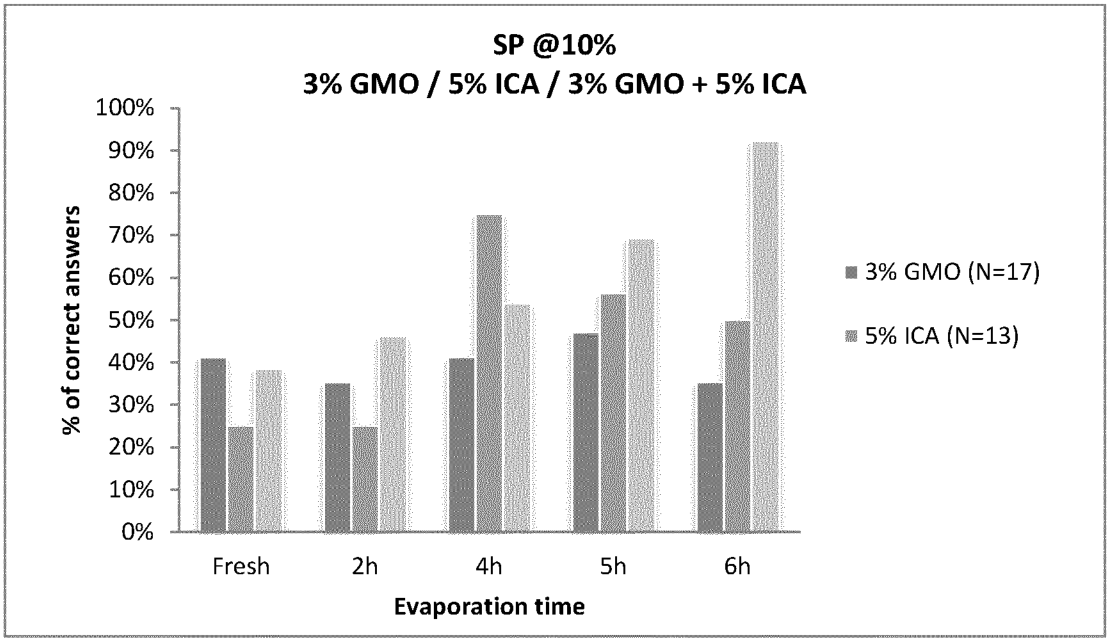
FIG. 4 is a bar graph showing results from a sensory panel comparison of Fragrance SP in EDT without and with 3% GMO, Fragrance SP in EDT without and with 5% ICA, and Fragrance SP in EDT without and with 3% GMO+5% ICA. There was no difference with 3% GMO; there was a significant difference with 5% ICA at 4 and 5 hours; and there was a significant difference with 3% GMO+5% ICA at 5 and 6 hours.

The results presented in FIG. 4 show:

with 3% GMO: no difference, with 5% ICA: significant difference at 4 and 5 hours, with 3% GMO+5% ICA: significant difference at 5 and 6 hours.

There was a higher performance of the formulation containing the mixture of GMO-ICA after 5 hours of evaporation.

The same experiment was done with a mixture of GMO and Hedione.

Sensory panels were performed in order to compare:

Fragrance SP in EDT without and with 3% GMO (Table 6)

Fragrance SP in EDT without and with 5% Hedione (Table 7).

Fragrance SP in EDT without and with 3% GMO+5% Hedione (Table 8)

Figure 5:
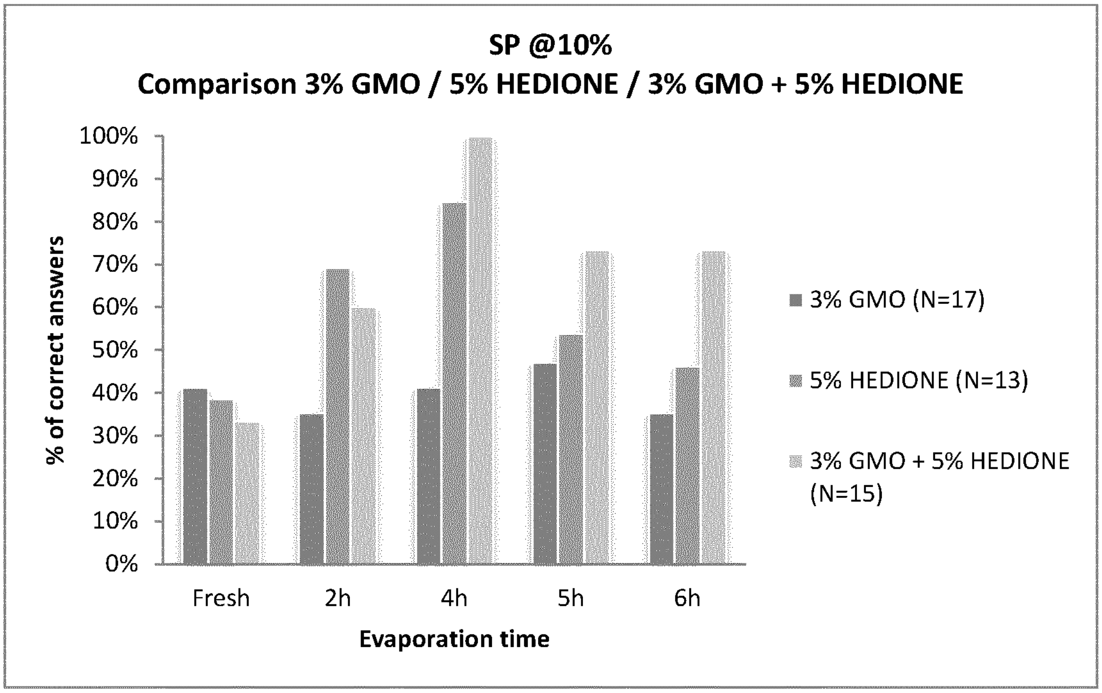
FIG. 5 is a bar graph showing the results from a sensory panel comparison using a mixture of GMO and Hedione. Sensory panels compared Fragrance SP in EDT without and with 3% GMO; Fragrance SP in EDT without and with 5% Hedione; and Fragrance SP in EDT without and with 3% GMO+5% Hedione. There was no difference with 3% GMO, there was a significant difference from 2 to 4 hours with 5% Hedione, there was a significant difference from 2 to 6 hours with 3% GMO+5% Hedione: significant difference. There was a higher performance of the formulation containing the mixture GMO-Hedione after 2 hours of evaporation.

The results presented in FIG. 5 show:

with 3% GMO: no difference, with 5% Hedione: significant difference from 2 to 4 hours, with 3% GMO+5% Hedione: significant difference from 2 to 6 hours.

There was a higher performance of the formulation containing the mixture GMO-Hedione after 2 hours of evaporation.

5) Examples of Synergistic Mixtures

Figure 6:
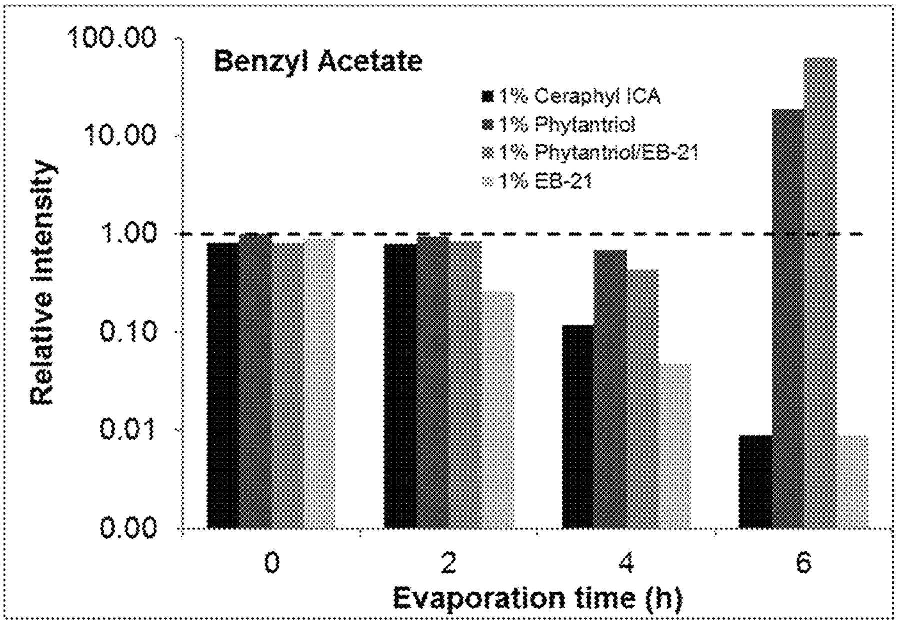
FIGS. 6 *a* and *b* are bar graphs showing the performance of two highly volatile fragrance ingredients, benzyl acetate and dihydromyrcenol, after evaporation at 2, 4 and 6 hours and compared it to the performance of the reference sample EDT0 (value 1). The intensity of the fragranced ingredients after 6 hours of evaporation was significantly higher in the presence of phytantriol and the mixture of phytantriol and gelator.
Figure 6:
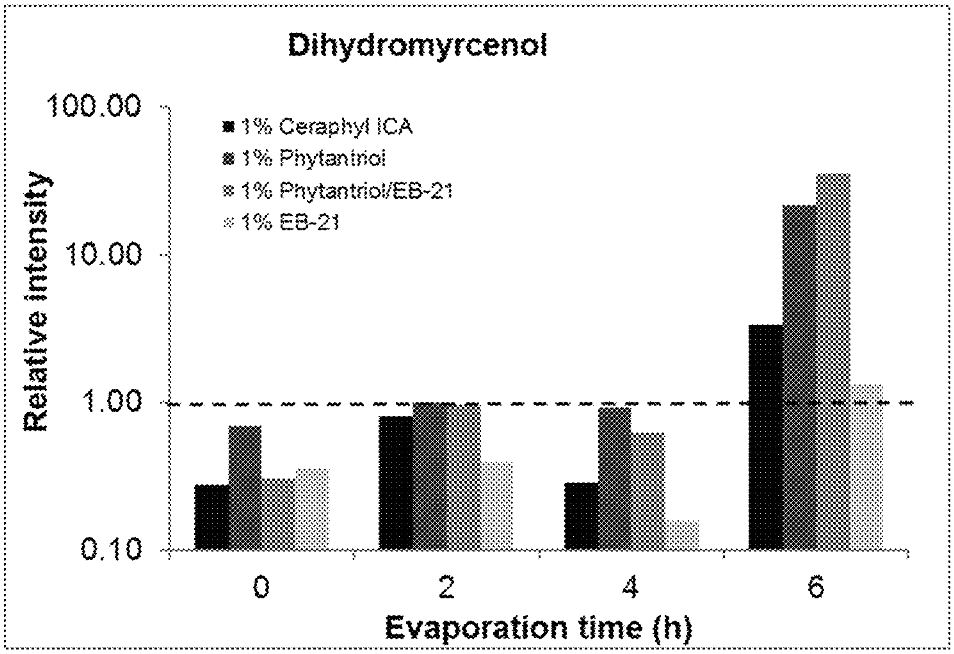

Mixtures of the amphiphilic oil-soluble compound (phytantriol) and a fixative (ICA) or a gelator (EB-21) were prepared and integrated in ethanol-water solutions having the proportions shown in Table 2. The performance of two highly volatile fragrance ingredients: benzyl acetate and dihydromyrcenol, were followed after evaporation at 2, 4 and 6 hours and compared to the performance of the reference sample EDT0 (value 1). The intensity of the fragranced ingredients after 6 hours of evaporation was significantly higher in presence of phytantriol and the mixture of phytantriol and gelator. See FIG. 6.

Figure 7:
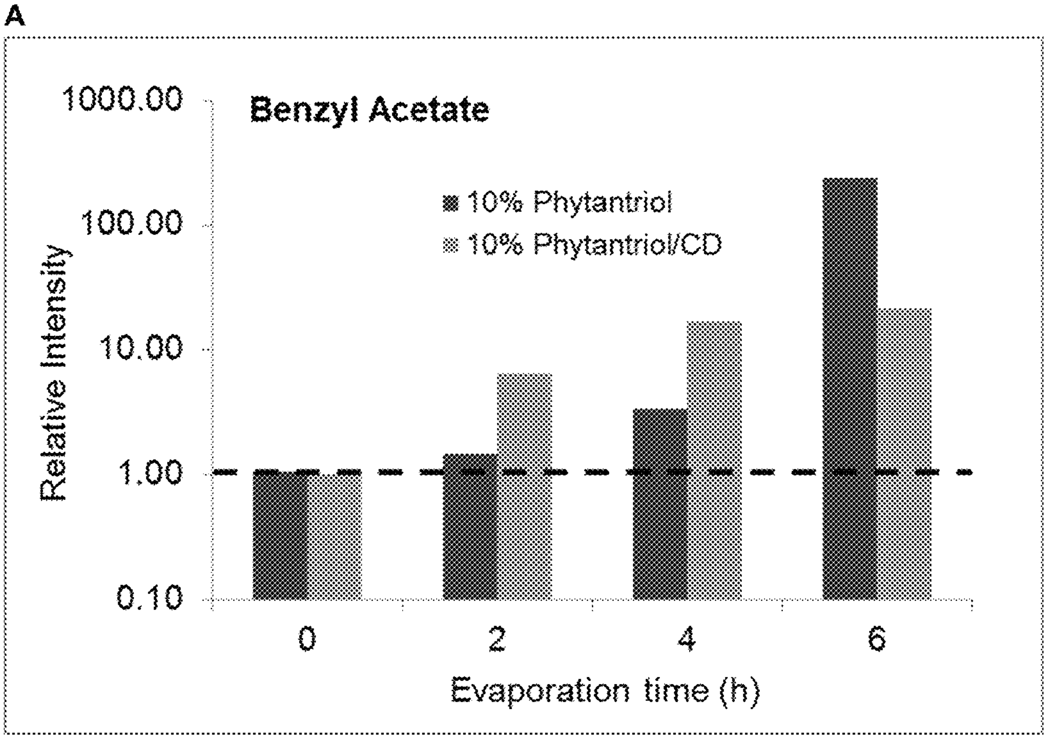
FIGS. 7 *a* and *b* are bar graphs showing the intensity of (A) benzyl acetate with 10% phytantriol, and benzyl acetate with 10% phytantriol and β-cyclodextrin (CD); and (B) dihydromyrcenol with 10% phytantriol, and dihydromyrcenol with 10% phytantriol and β-cyclodextrin.
Figure 7:
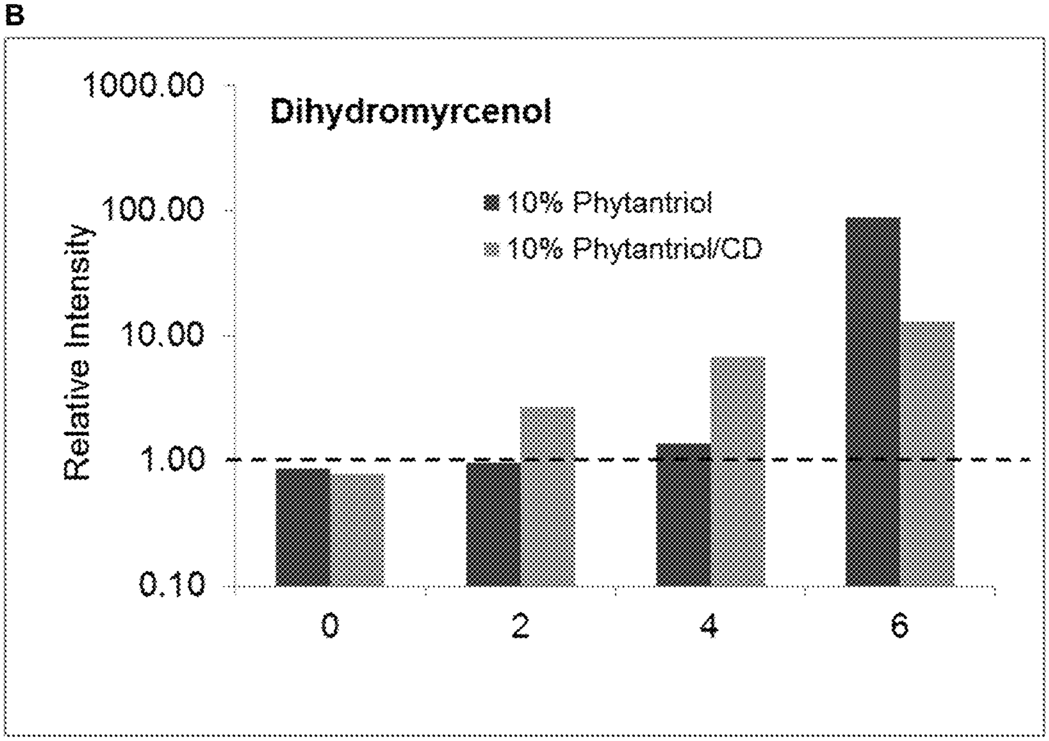
Figure 8:
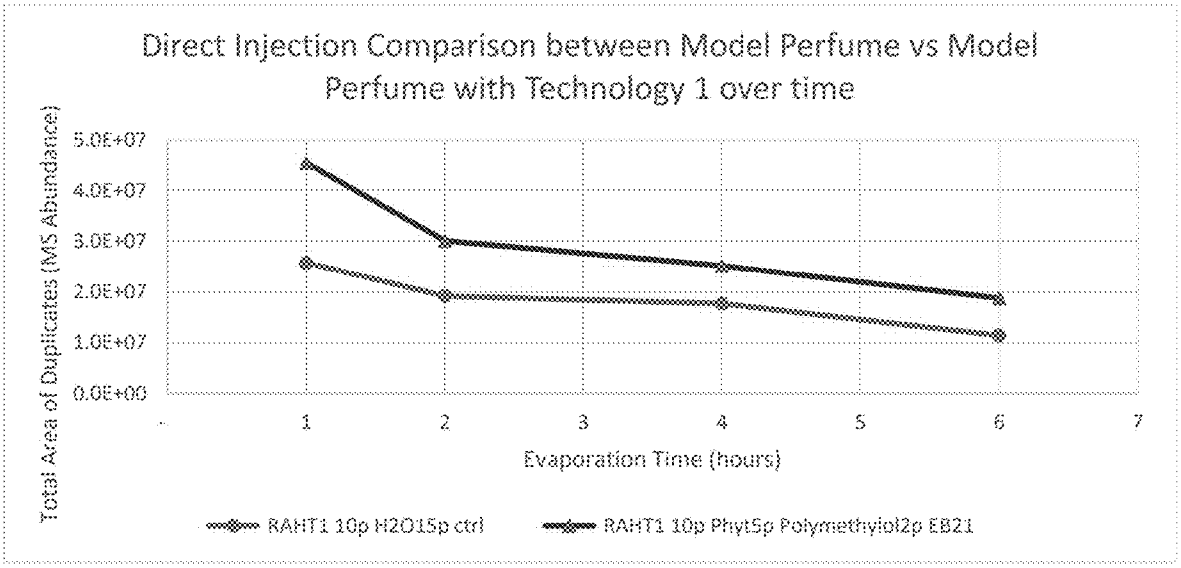
FIG. 8 is a graph showing the total area sums throughout evaporation of 5% Phytantriol 2% Polymethylol and 0.3% EB21 with Research Accord HT1 formula vs. RAHT1 formula alone. The data shows a higher retention of the sum of all compounds with 5% Phytantriol 2% Polymethylol and 0.3% EB21 throughout the entire evaporation against the control.
Figure 9:
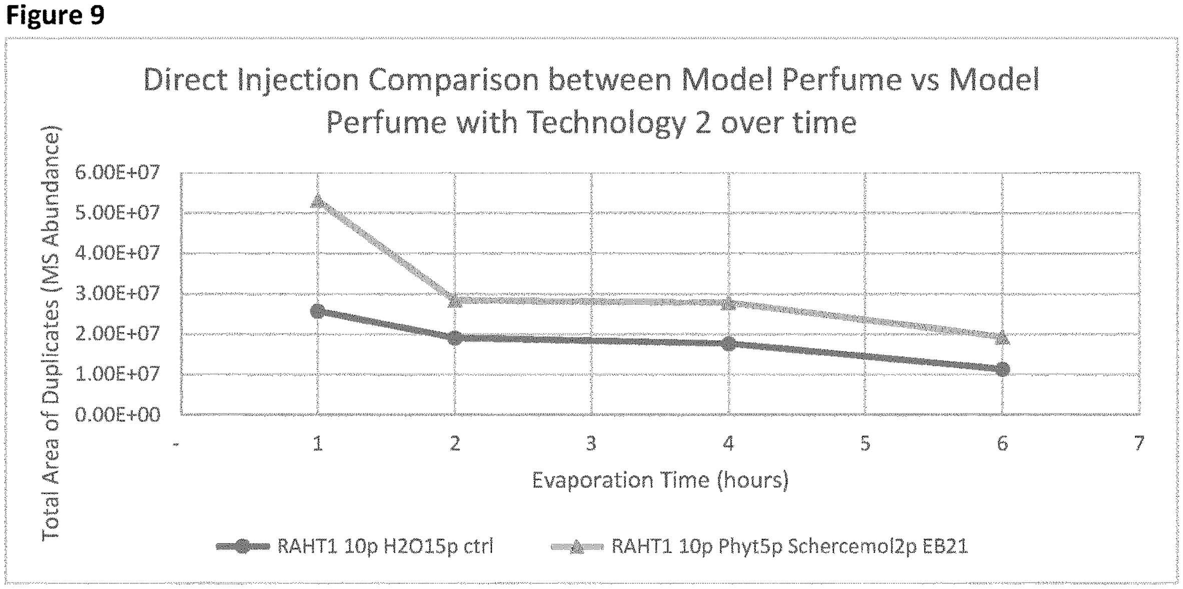
FIG. 9 is a graph showing total area sums throughout evaporation of 5% Phytantriol 2% Schercemol and 0.3% EB21 with Research Accord HT1 formula vs. RAHT1 formula alone. The data shows a higher retention of the sum of all compounds with 5% Phytantriol 2% Schercemol and 0.3% EB21 throughout the entire evaporation against the control.
Figure 10:
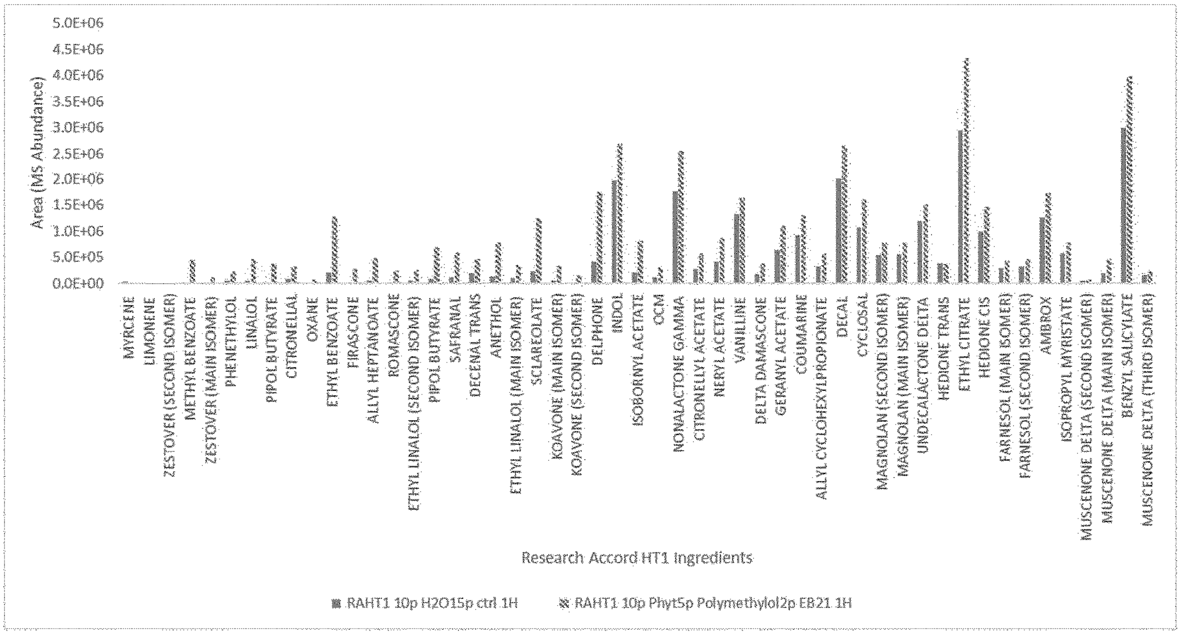
FIG. 10 is a graph showing direct injection data at 1 hour evaporation of 5% Phytantriol 2% Polymethylol and 0.3% EB21 with Research accord HT1 formula vs. HT1 formula alone. The data shows a higher retention of all compounds and most noticeably high and mid volatility notes on the left.
Figure 11:
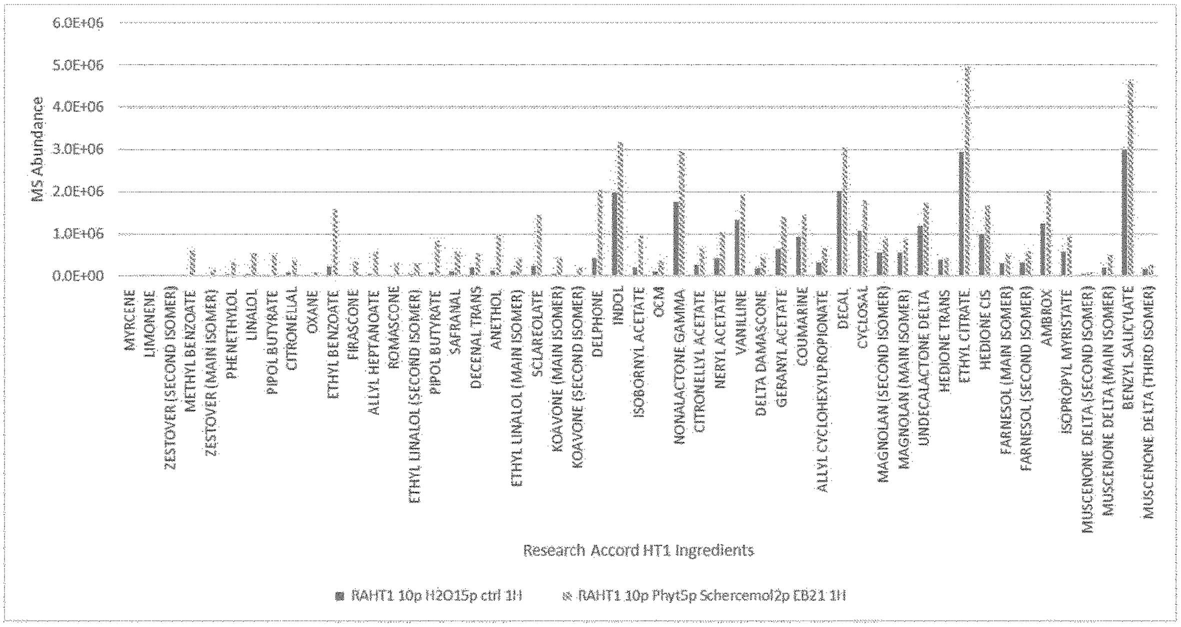
FIG. 11 is a graph showing direct Injection data at 1 hour evaporation of 5% Phytantriol 2% Schercemol and 0.3% EB21 with Research accord HT1 formula vs. HT1 formula alone. The data shows a higher retention of all compounds and most noticeably high and mid volatility notes on the left.
Figure 12:
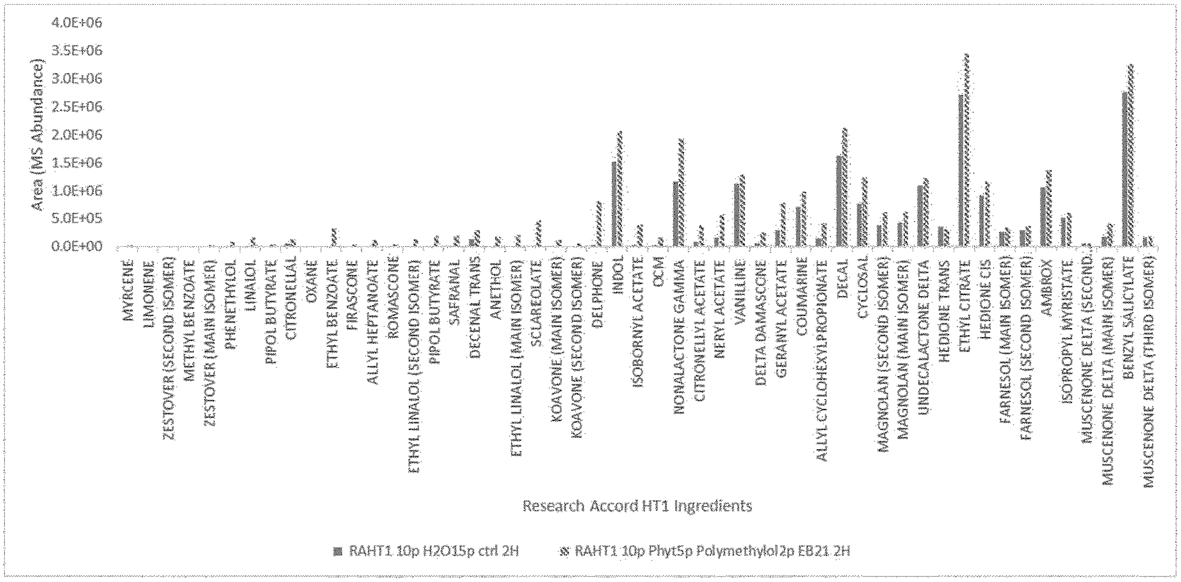
FIG. 12 is a graph showing direct Injection data at 2 hours evaporation of 5% Phytantriol 2% Polymethylol and 0.3% EB21 with Research accord HT1 formula vs. HT1 formula alone. The data shows a higher retention of all compounds and most noticeably high and mid volatility notes on the left.
Figure 13:
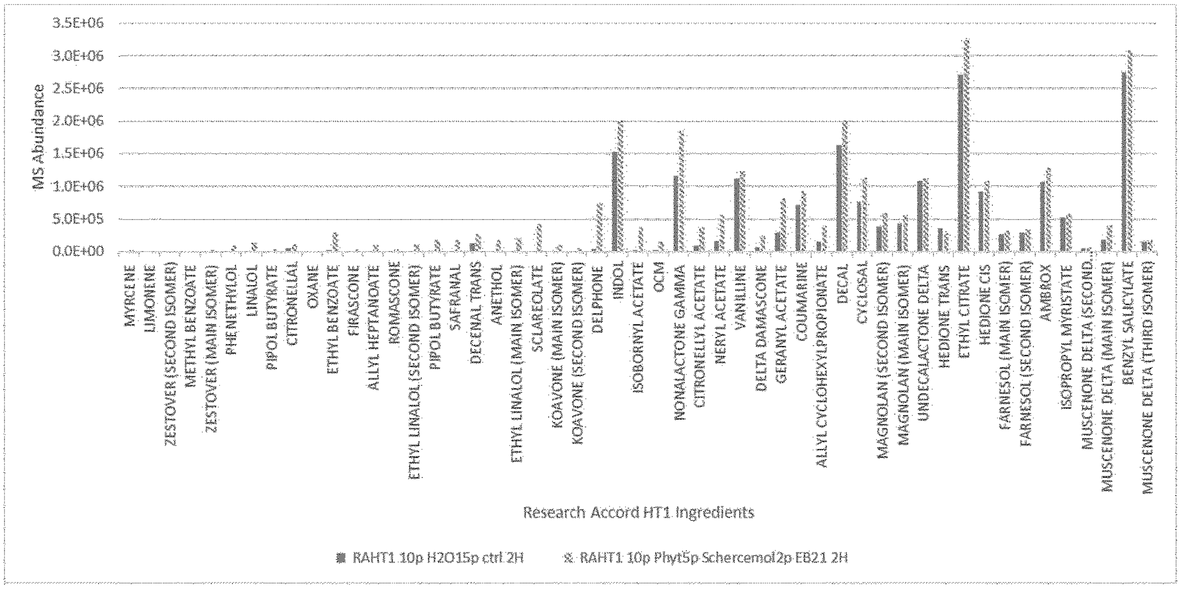
FIG. 13 is a graph showing direct Injection data at 2 hours evaporation of 5% Phytantriol 2% Schercemol and 0.3% EB21 with Research accord HT1 formula vs. HT1 formula alone. The data shows a higher retention of all compounds and most noticeably high and mid volatility notes on the left.
Figure 14:
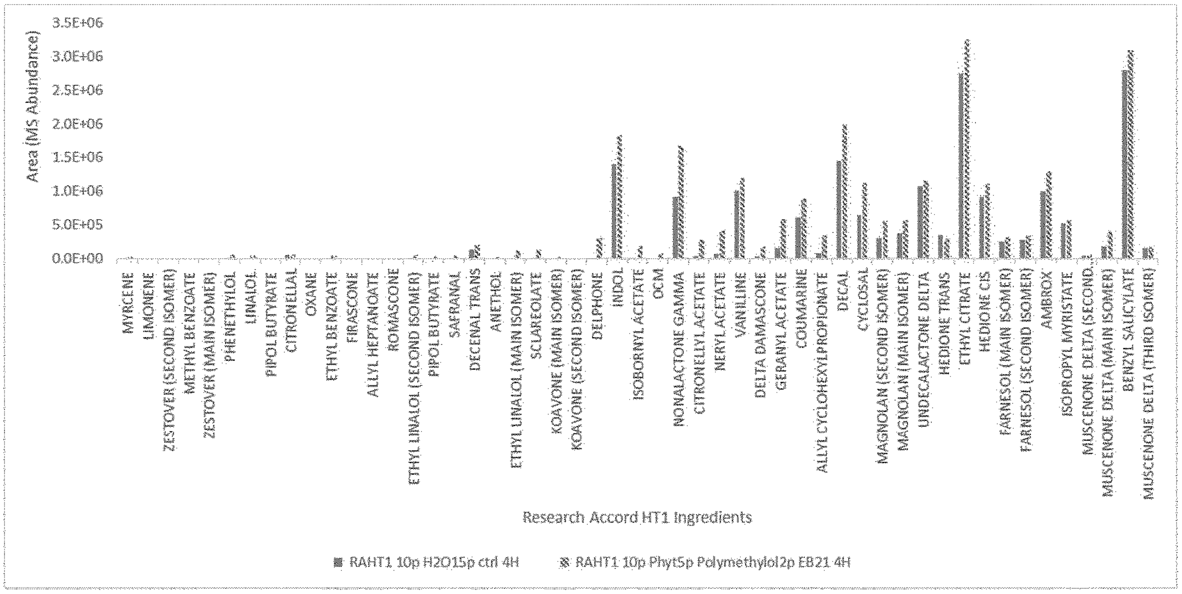
FIG. 14 is a graph showing direct Injection data at 4 hours evaporation of 5% Phytantriol 2% Polymethylol and 0.3% EB21 with Research accord HT1 formula vs. HT1 formula alone. The data shows a higher retention of all compounds—most noticeably mid and low volatility notes on the right—even after most of the high volatility notes on the left has evaporated by 4 hours.
Figure 15:
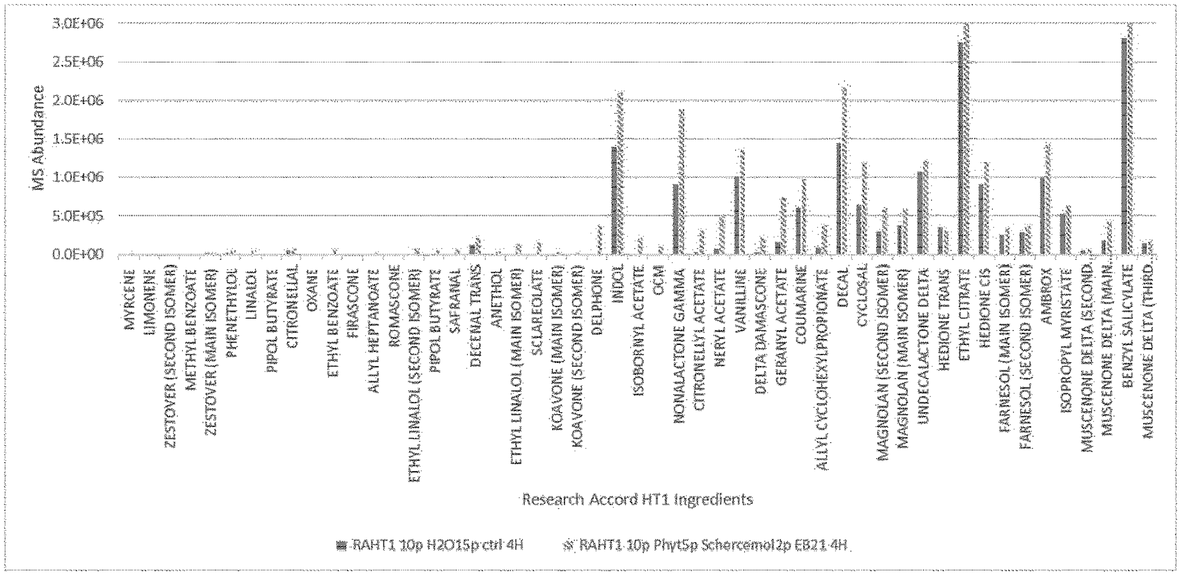
FIG. 15 is a graph showing direct Injection data at 4 hours evaporation of 5% Phytantriol 2% Schercemol and 0.3% EB21 with Research accord HT1 formula vs. HT1 formula alone. The data shows a higher retention of all compounds—most noticeably mid and low volatility notes on the right—even after most of the high volatility notes on the left has evaporated by 4 hours.
Figure 16:
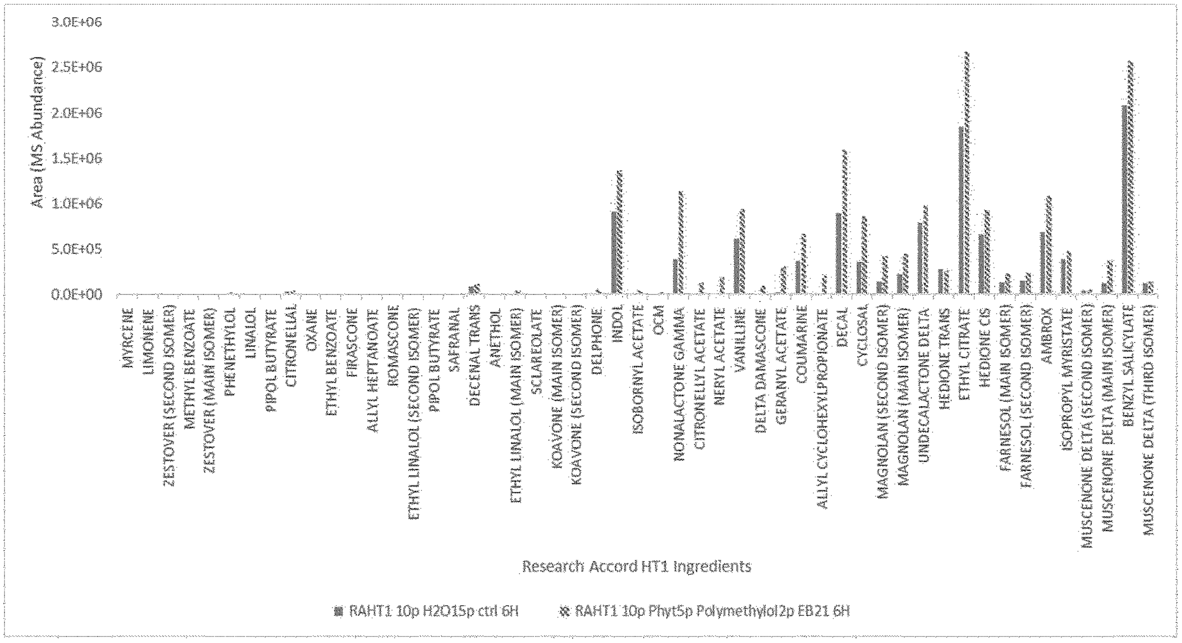
FIG. 16 is a graph showing direct injection data at 6 hours evaporation of 5% Phytantriol 2% Polymethylol and 0.3% EB21 with Research accord HT1 formula vs. HT1 formula alone. The data shows a higher retention of all compounds—most noticeably mid and low volatility notes on the right—even after the high volatility notes on the left has evaporated by 6 hours.
Figure 17:
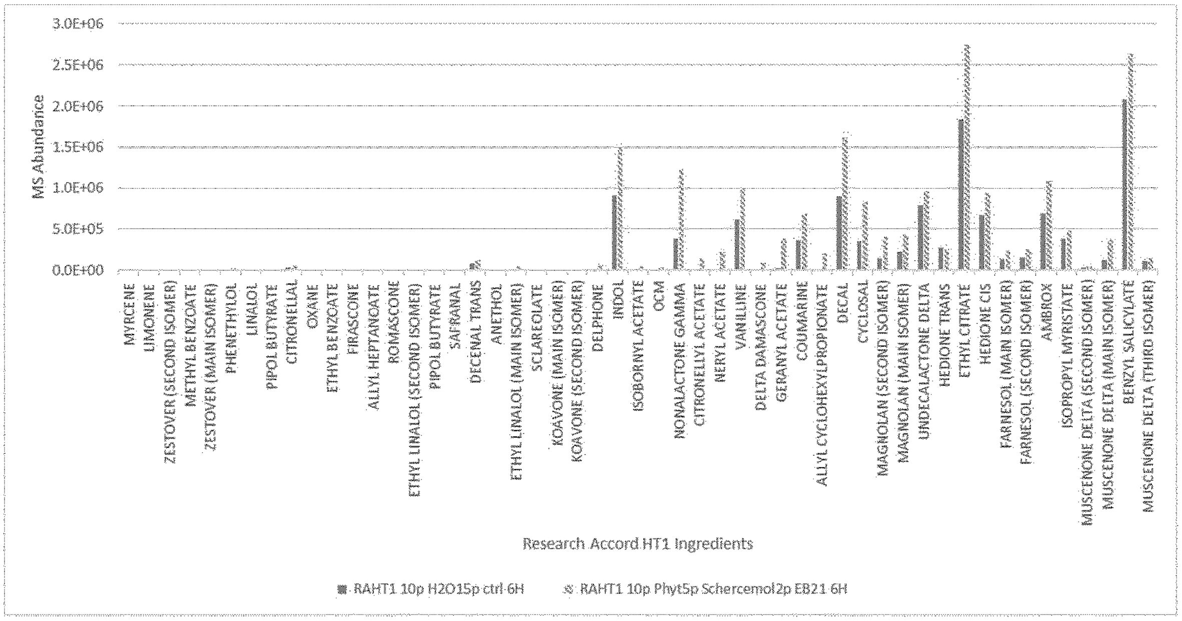
FIG. 17 is a graph showing direct injection data at 6 hours evaporation of 5% Phytantriol 2% Schercemol and 0.3% EB21 with Research accord HT1 formula vs. HT1 formula alone. The data shows a higher retention of all compounds—most noticeably mid and low volatility notes on the right—even after the high volatility notes on the left has evaporated by 6 hours.

Mixtures of (A) benzyl acetate with 10% phytantriol, and benzyl acetate with 10% phytantriol and β-cyclodextrin (CD); and (B) dihydromyrcenol with 10% phytantriol, and dihydromyrcenol with 10% phytantriol and CD were prepared and integrated in ethanol-water solutions having the proportions mentioned in Table 2. The performance of the two highly volatile fragrance ingredients: benzyl acetate and dihydromyrcenol, were followed after evaporation at 2, 4 and 6 hours. The intensity was greater for the mixtures containing CD. See FIG. 7.

Mixtures of the fragrances SP and LS with GMO combined with a modulator and a gelator were prepared and integrated in ethanol-water solutions having the proportions mentioned in Table 9, 10 and 11. At different moments t=0 min (Fresh), 4 hours and 6 hours, the randomized glass plates were evaluated by 7 panelists. The results presented in the Table 16 show higher performance of the formulations according to the present invention compared to control after 4 hours of evaporation for both fragrances SP and LS.

The combination 3% GMO, 1% Nerolidol and 0.3% EB-21 was the most efficient as it allowed higher performance after 4 hours and 6 hours for both fragrances SP and LS.

Lower p-values on fragrance LS compared to SP show a better performance of LS, which may be linked to its fragrance architecture that contains higher amount of heart notes.

TABLE 16

| Fragrance | Fragrance architecture | Samples | N* | p-value Fresh | 4 h | 6 h |
|---|---|---|---|---|---|---|
| SP | 28.5% > 0.08 torr 16.5% 0.0008-0.08 torr [45% > 0.0008 Torr] 55% < 0.0008 torr | SP @10% (ref) vs SP @10% + 3% GMO + 1% Nerolidol + 0.3% EB-21 | 7 | 1.0000 | 0.1733 | 0.0453 |
| SP | 28.5% > 0.08 torr 16.5% 0.0008-0.08 torr [45% > 0.0008 Torr] 55% < 0.0008 torr | SP @10% (ref) vs SP @10% + 3% GMO + 1% Nerolidol + 1% Polymethylol + 0.3% EB-21 | 7 | 0.7366 | 0.0453 | 0.7366 |
| SP | 28.5% > 0.08 torr 16.5% 0.0008-0.08 torr [45% > 0.0008 Torr] 55% < 0.0008 torr | SP @10% (ref) vs SP @10% + 3% GMO + 2% Polymethylol + 0.3% EB-21 | 7 | 0.4294 | 0.0453 | 0.1733 |
| LS | 14.5% > 0.08 torr 37.5% 0.0008-0.08 torr [52% > 0.0008 Torr] 48% < 0.0008 torr | LS @10% (ref) vs SP @10% + 3% GMO + 1% Nerolidol + 0.3% EB-21 | 7 | 0.7366 | 0.0453 | 0.0069 |
| LS | 14.5% > 0.08 torr 37.5% 0.0008-0.08 torr [52% > 0.0008 Torr] 48% < 0.0008 torr | LS @10% (ref) vs LS @10% + 3% GMO + 1% Nerolidol + 1% Polymethylol + 0.3% EB-21 | | 0.4294 | 0.0453 | 0.0453 |

*N = Number of panelists

Influence of Fragrance Construction

Sensory panels evaluated model fragrances having different constructions which vary from a typical pyramid architecture (middle volatility components present in a greater amount than the low and high volatility components) were tested in sensory panel in the presence of GMO solutions.

The results presented on Table 17 show that performance with GMO was dependent on the fragrance construction based on the volatility of the perfume's raw materials The results shown below were based on perceived intensity of a panel for Fragrance at 10% in presence of 3% GMO VS Fragrance at 10% alone. The improved performance was noted with % of correct answers >55% with included significance listed (p-value)

TABLE 17

| Fragrance | Samples | N | p-value Fresh | 2 h | 4 h | 5 h | 6 h |
|---|---|---|---|---|---|---|---|
| A | 10.7% > 0.08 torr 22.3% 0.0008-0.08 torr [33% > 0.0008 Torr] 67% < 0.0008 torr | 20 | 0.9997 | 0.3385 | 0.9824 | 0.9396 | 0.3385 |
| B | 53.7% > 0.08 torr 21.3% 0.0008-0.08 torr [75% > 0.0008 torr] 25% < 0.0008 torr | 15 | 0.0085 | 0.3816 | 0.2030 | 0.0018 | <0.0001 |
| C | 43.7% > 0.08 torr 16.3% 0.0008-0.08 torr 60% > 0.0008 torr] 40% < 0.0008 torr | 17 | 0.0019 | 0.3261 | <0.0001 | 0.0019 | 0.0003 |
| D | 29.7% > 0.08 torr 40.3% 0.0008-0.08 torr [70% > 0.0008 torr] 30% < 0.0008 torr | 10 | 0.7009 | 0.0004 | <0.0001 | <0.0001 | <0.0001 |

Perfumery rules impart extra-improved performance and include a fragrance component as follows:

A volatility component in an amount from 35% to 100 wt % of the fragrance component, comprising at least one perfume raw material having a first vapor pressure greater than 0.0008 Torr at 22° C.;

And, within the perfume constructions above:

Construction 1—A volatility component from 40 to 100 wt % of the fragrance component comprising at least one perfume raw material having a first vapor pressure greater than 0.08 torr and optionally, a second at least one perfume raw material having a first vapor pressure greater than 0.08 Torr at 22° C.;

Construction 2—A volatility component in an amount from 0.08 to 85 wt % of the fragrance component, comprising a first at least one perfume raw material having a first vapor pressure range of 0.0008 to 0.08 Torr at 22° C.; and, optionally, a second at least one perfume raw material having a first vapor pressure range of 0.0008 to 0.08 Torr at 22° C.;

c) Conclusion

The comparison of these different evaporation kinetics shows that formulations of the present invention have higher fragrance retention than a standard Eau de toilette composition. The fragrance retention is significant in the EdT formulations containing amphiphilic oil-soluble compounds of the present invention (phytantriol) and low molecular weight gelators. The long-lasting performance of the invention against the standard EdT formulation was confirmed 4-6 h after the deposition. Synergistic mixtures were discovered surprisingly providing better fragrance retention.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A long-lasting fragrance composition comprising:

a. a fragrance oil, b. 0.01% to 40% w/w of the long-lasting fragrance composition of an amphiphilic oil-soluble compound, c. a volatile solvent, and d. water;

wherein the long-lasting fragrance composition further comprises a gelator, wherein the gelator is selected from the group consisting of: an n-alkane having a greater than 16 length CH2 chain, a hydroxyalkanoic acid, hydroxy-octadecanoyl, hydroxy-hexadecanoyl, a dihydroxyalkanoic acid, a dicarboxylic acid, a fatty acids alkyl ester with an alkyl chain length greater than 20 CH2 groups, a hydroxyalkanoic alcohol, a glycyrrhizic acid, caffeine, an anthryl derivatives, dendrimers n-alkanes, oligo(p-phenylenevinylene), dipyridylurea-carboxylic acid combination, diamine linked Dendron, dibutyl ethylhexanoyl glutamide, dibutyl lauroyl monoglycerol, dibutyl lauroyl 2-glycerol, dibutyl lauroyl glycerate, dibutyl lauroyl glyceryl ether, dibutyl lauroyl monoethanolamide, dibutyl lauroyl diethanolamide, dibutyl lauroyl glutamide, an organogelator, an amino acid-based gelator, a hydroxyfatty acid gelator, ester gum, and combinations thereof.

2. The long-lasting fragrance composition of claim 1, wherein the amphiphilic oil-soluble compound is 0.5% to 30% w/w of the long-lasting fragrance composition.

3. The long-lasting fragrance composition of claim 1, wherein the wherein the amphiphilic oil-soluble compound includes a compound having one of the following chemical structures:

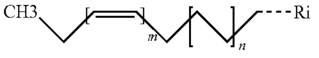

or

-continued

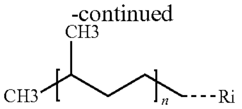

where n represents the number of CH2 groups and is greater than 14 and m represents the number of unsaturated C—C bounds and is greater than or equal to 1, and Ri is selected from the group consisting of:

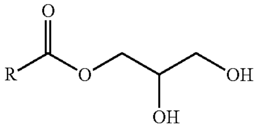

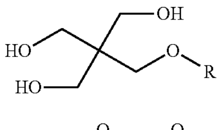

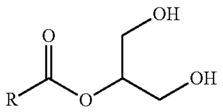

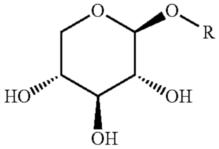

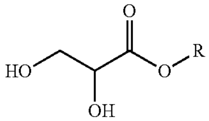

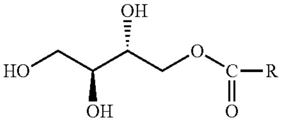

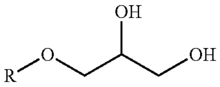

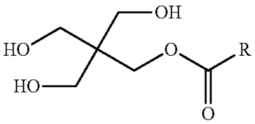

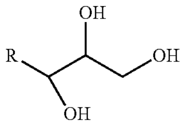

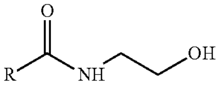

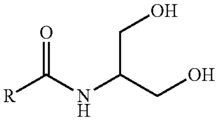

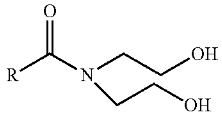

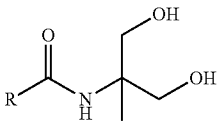

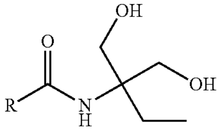

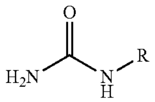

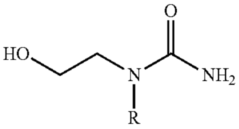

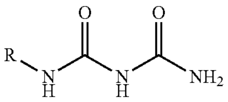

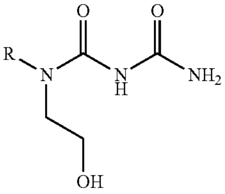

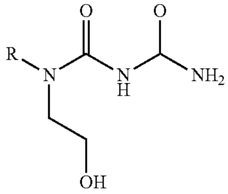

-continued

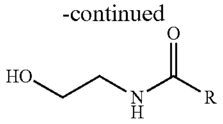

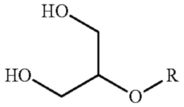

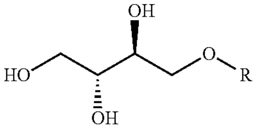

serinolamide, methylpropanediolamide, ethylpropanediolamide, urea, a urea alcohol, biuret, a biuret alcohol, anandamine, glycerol ether, a glycolipid, and a combination thereof.

4. The long-lasting fragrance composition of claim 1, wherein the gelator is 0.01 to 15% w/w of the long-lasting fragrance composition.

5. The long-lasting fragrance composition of claim 4, wherein the gelator is 0.3 to 0.6% w/w of the long-lasting fragrance composition.

6. The long-lasting fragrance composition of claim 1, wherein the water is 0.01 to 60% w/w of the long-lasting fragrance composition.

7. The long-lasting fragrance composition of claim 1, wherein the volatile solvent is selected from the group consisting of: ethanol, isopropyl alcohol, an ether, and mixtures thereof.

8. The long-lasting fragrance composition of claim 1, further comprising a modulator.

9. The long-lasting fragrance composition of claim 8, wherein the modulator is selected from the group consisting of: methyl glucoside polyol; ethyl glucoside polyol; propyl glucoside polyol; isocetyl alcohol; PPG-3 myristyl ether; neopentyl glycol diethylhexanoate; sucrose laurate; sucrose dilaurate; sucrose myristate; sucrose palmitate; sucrose stearate; sucrose distearate; sucrose tristearate; hyaluronic acid disaccharide sodium salt; sodium hyaluronate; propylene glycol propyl ether; dicetyl ether; polyglycerin-4 ethers; isoceteth-5; isoceteth-7; isoceteth-10; isoceteth-12; isoceteth-15; isoceteth-20; isoceteth-25; isoceteth-30; disodium lauroamphodipropionate; hexaethylene glycol monododecyl ether; neopentyl glycol diisononanoate; cetearyl ethylhexanoate; panthenol ethyl ether; DL-panthenol; N-hexadecyl n-nonanoate; noctadecyl n-nonanoate; nerolidol; polymethylol; a profragrance; a cooling agent; a cyclodextrin; an encapsulation; a fatty acid; oleic acid; a fatty alcohol; oleic alcohol; a polyglyceride fatty acid; diglycerol oleate; and a combination thereof.

10. The long-lasting fragrance composition of claim 1, wherein the amphiphilic oil-soluble compound is glycerol monooleate or phytantriol or a combination thereof.

11. The long-lasting fragrance composition according to claim 8 wherein the modulator is nerolidol.

12. The long-lasting fragrance composition of claim 8, which comprises:

1% to 10% w/w of the composition of the amphiphilic oil-soluble compound;

0.5% to 15% w/w of the composition of the modulator, 0.1% to 10% w/w of the composition of the gelator, and 1% to 40% w/w of the composition of water.

13. The long-lasting composition of claim 12 wherein the amphiphilic oil-soluble compound is glycerol monooleate, the gelator is dibutylhexanyl glutamide, and the modulator is selected from the group consisting of: nerolidol, polymethylol, and a combination thereof.

14. The long-lasting fragrance composition of claim 1, wherein 40 to 100% of the fragrance oil is a volatility component comprising at least one perfume raw material having a vapor pressure greater than 0.0008 Torr at 22° C.

15. The long-lasting fragrance composition of claim 14, wherein the volatility component comprises at least one perfume raw material having a vapor pressure greater than 0.08 torr.

16. The long-lasting fragrance composition of claim 15, further comprising a second perfume raw material having a vapor pressure greater than 0.08 Torr at 22° C.

17. The long-lasting fragrance composition of claim 15, wherein 0.08 to 85% of the fragrance oil is a volatility component comprising at least one perfume raw material having a vapor pressure in the range of 0.0008 to 0.08 Torr at 22° C.

18. The long-lasting fragrance composition of claim 17, further comprising a second perfume raw material having a vapor pressure in the range of 0.0008 to 0.08 Torr at 22° C.

19. A leave-on volatile solvent-containing consumer product comprising the long-lasting fragrance composition of claim 1.

* * * * *